(12) United States Patent
Tajima

(10) Patent No.: US 10,005,594 B2
(45) Date of Patent: Jun. 26, 2018

(54) DEFORMING ELEMENT-INCLUDED DISPENSING TIP, DEFORMING ELEMENT-INCLUDED DISPENSING DEVICE, AND DEFORMING ELEMENT-INCLUDED DISPENSING PROCESSING METHOD

(71) Applicant: Universal Bio Research Co., Ltd., Matsudo-shi, Chiba (JP)

(72) Inventor: Hideji Tajima, Matsudo (JP)

(73) Assignee: UNIVERSAL BIO RESEARCH CO., LTD., Matsudo-shi Chiba (JP)

( * ) Notice: Subject to any disclaimer, the term of this patent is extended or adjusted under 35 U.S.C. 154(b) by 424 days.

(21) Appl. No.: 14/424,075

(22) PCT Filed: Sep. 2, 2013

(86) PCT No.: PCT/JP2013/073513
§ 371 (c)(1),
(2) Date: Feb. 26, 2015

(87) PCT Pub. No.: WO2014/034928
PCT Pub. Date: Mar. 6, 2014

(65) Prior Publication Data
US 2015/0210437 A1 Jul. 30, 2015

(30) Foreign Application Priority Data

Aug. 31, 2012 (JP) .................................. 2012-192519
Jun. 14, 2013 (JP) .................................. 2013-126057

(51) Int. Cl.
*B65D 35/30* (2006.01)
*B01L 3/02* (2006.01)
(Continued)

(52) U.S. Cl.
CPC ............ *B65D 35/30* (2013.01); *B01L 3/0275* (2013.01); *B65D 35/02* (2013.01);
(Continued)

(58) Field of Classification Search
USPC ......................................................... 422/515
See application file for complete search history.

(56) References Cited

U.S. PATENT DOCUMENTS

| 4,444,062 A | 4/1984 | Bennett et al. |
| 4,511,534 A * | 4/1985 | Bennett, Jr. ............. B01L 3/021 |
| | | 141/238 |

(Continued)

FOREIGN PATENT DOCUMENTS

| JP | 551371162 | 3/1980 |
| JP | 373995362 | 9/1999 |

OTHER PUBLICATIONS

International Search Report and Written Opinion regarding PCT/JP2013/73513 issued by the International Search Authority, dated Oct. 29, 2013, 3 pages.

(Continued)

*Primary Examiner* — Jill A Warden
*Assistant Examiner* — Brittany I Fisher
(74) *Attorney, Agent, or Firm* — Haynes and Boone, LLP

(57) ABSTRACT

It is an object to provide a deforming element-included dispensing tip, a deforming element-included dispensing device, and a deforming element-included dispensing processing method not requiring any cylinder and capable of achieving highly precise position control and enhancing integration of higher density and reducing the burden in the quality control in reaction processing of a biological material for extraction of DNA and the like. A tip-shaped container formed with a non-deforming wall having an opening portion at an upper side and an inlet unit at a lower (Continued)

side for allowing fluid to flow in and flow out and a sealing plug attached to the opening portion so as to seal the opening portion are provided, and the sealing plug is configured to be provided with a deforming element.

4 Claims, 21 Drawing Sheets

(51) Int. Cl.
    *G01N 35/10*     (2006.01)
    *B65D 35/02*     (2006.01)
    *B01L 9/00*     (2006.01)
    *G01N 35/00*     (2006.01)

(52) U.S. Cl.
    CPC .......... *G01N 35/1074* (2013.01); *B01L 3/021* (2013.01); *B01L 9/543* (2013.01); *B01L 2200/0668* (2013.01); *B01L 2200/0689* (2013.01); *B01L 2300/0681* (2013.01); *B01L 2400/0481* (2013.01); *G01N 35/0098* (2013.01); *G01N 35/1016* (2013.01); *G01N 2035/1053* (2013.01)

(56) References Cited

U.S. PATENT DOCUMENTS

| | | | |
|---|---|---|---|
| 4,626,509 A * | 12/1986 | Lyman | C12M 29/00 222/43 |
| 4,852,620 A * | 8/1989 | Jakubowicz | B01L 3/021 141/114 |
| 5,154,702 A * | 10/1992 | Foyil | B01L 3/0282 215/214 |
| 5,786,265 A | 7/1998 | Hwang et al. | |
| 5,976,112 A * | 11/1999 | Lyza, Jr. | A61M 5/007 427/2.3 |
| 6,482,361 B1 * | 11/2002 | Suovaniemi | B01L 3/0217 422/525 |
| 6,499,364 B1 | 12/2002 | Suovaniemi | |
| 6,509,193 B1 | 1/2003 | Tajima | |
| 7,157,047 B2 | 1/2007 | Tajima | |
| 8,425,860 B2 | 4/2013 | Tajima | |
| 8,486,347 B2 | 7/2013 | Tajima | |
| 8,518,347 B2 | 8/2013 | Tajima | |
| 8,852,525 B2 | 10/2014 | Tajima | |
| 2001/0007770 A1 | 7/2001 | Tajima | |
| 2005/0118589 A1* | 6/2005 | Vann | B82Y 5/00 435/6.12 |
| 2006/0268276 A1 | 11/2006 | Tajima | |
| 2008/0193995 A1 | 8/2008 | Tajima | |
| 2010/0015010 A1 | 1/2010 | Tajima | |
| 2010/0018331 A1 | 1/2010 | Tajima et al. | |
| 2010/0278698 A1 | 11/2010 | Tajima | |
| 2011/0295212 A1* | 12/2011 | Greter | A61B 17/00491 604/191 |

OTHER PUBLICATIONS

Written Opinion regarding PCT/JP2013/73513 issued by the International Preliminary Examining Authority, dated Aug. 26, 2014, 4 pages.
International Preliminary Examination Report regarding PCT/JP2013/73513 issued by the International Preliminary Examining Authority, dated Nov. 27, 2014, 16 pages.

* cited by examiner

[Fig.1]
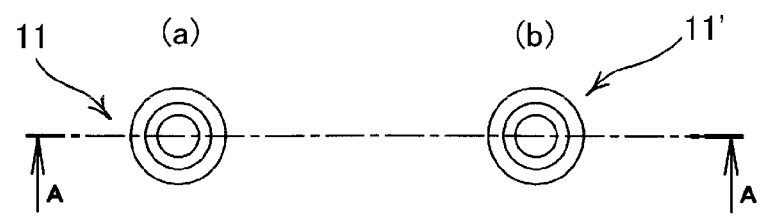
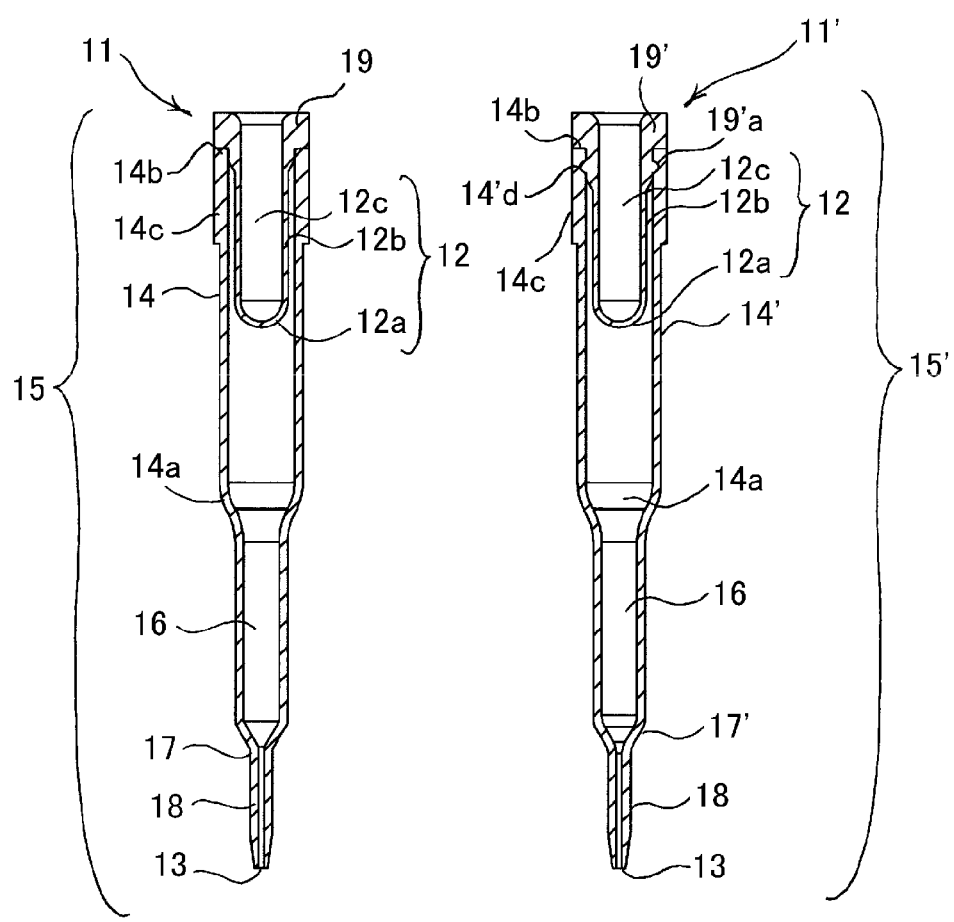

[Fig.2]
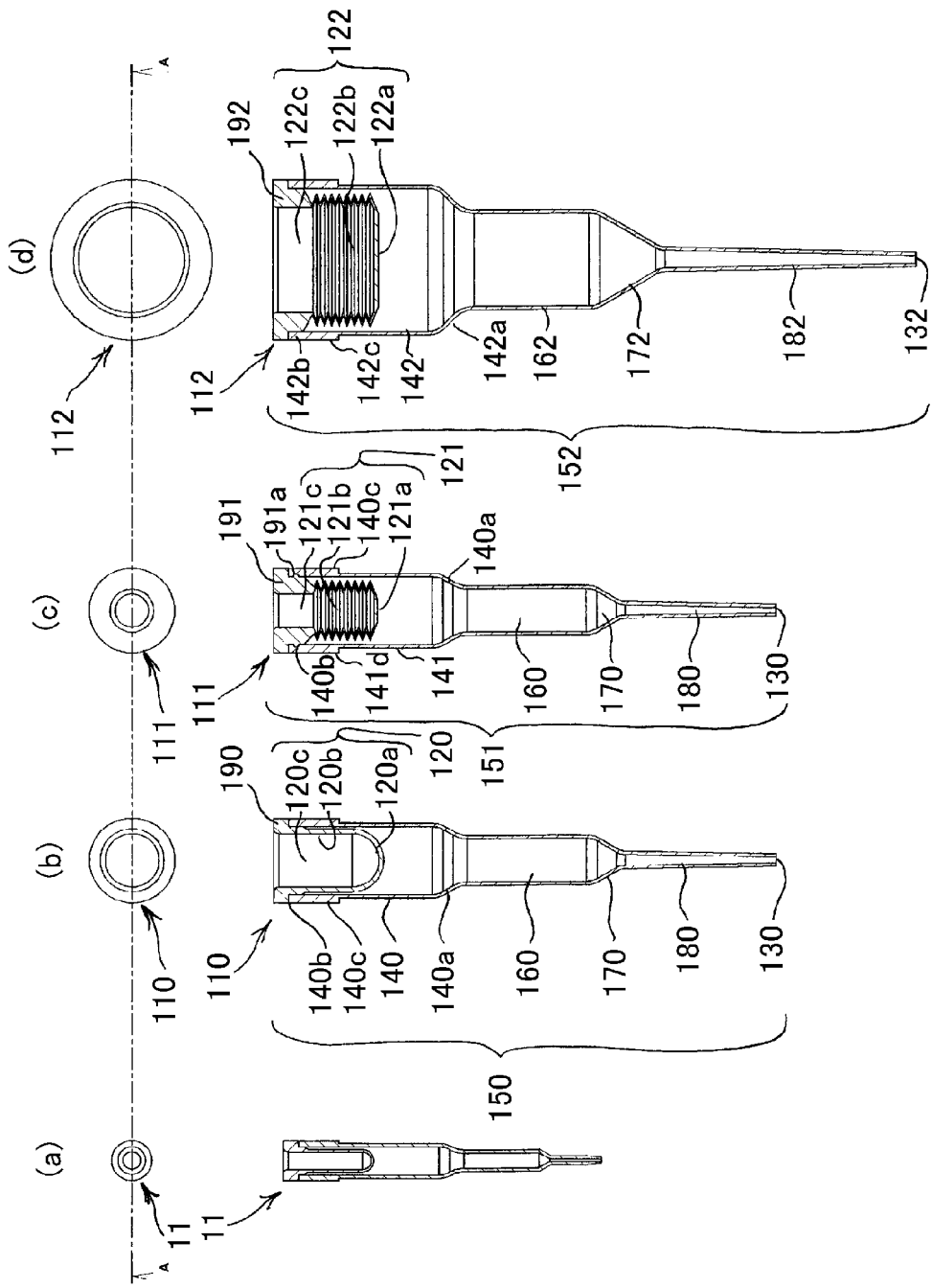

[Fig.3]
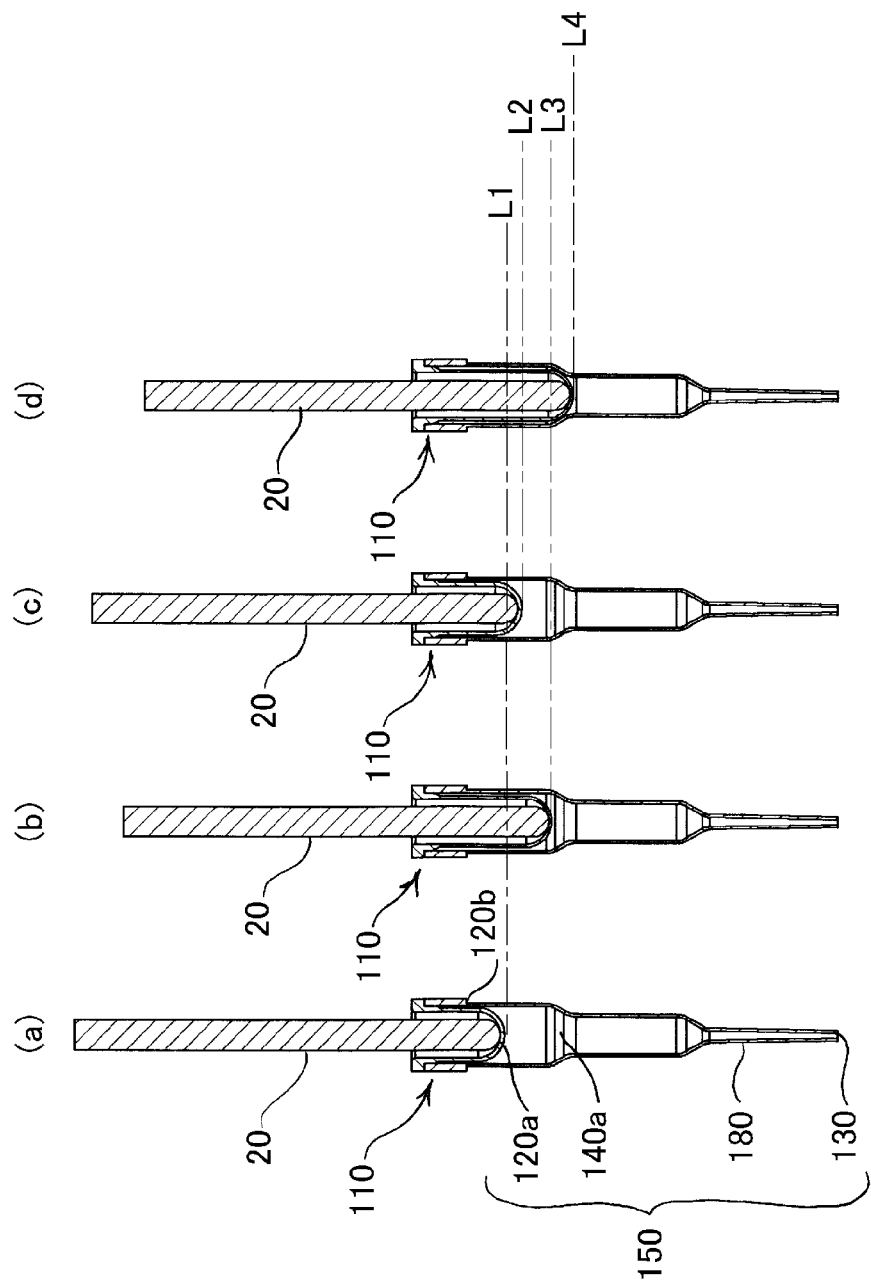

[Fig.4]
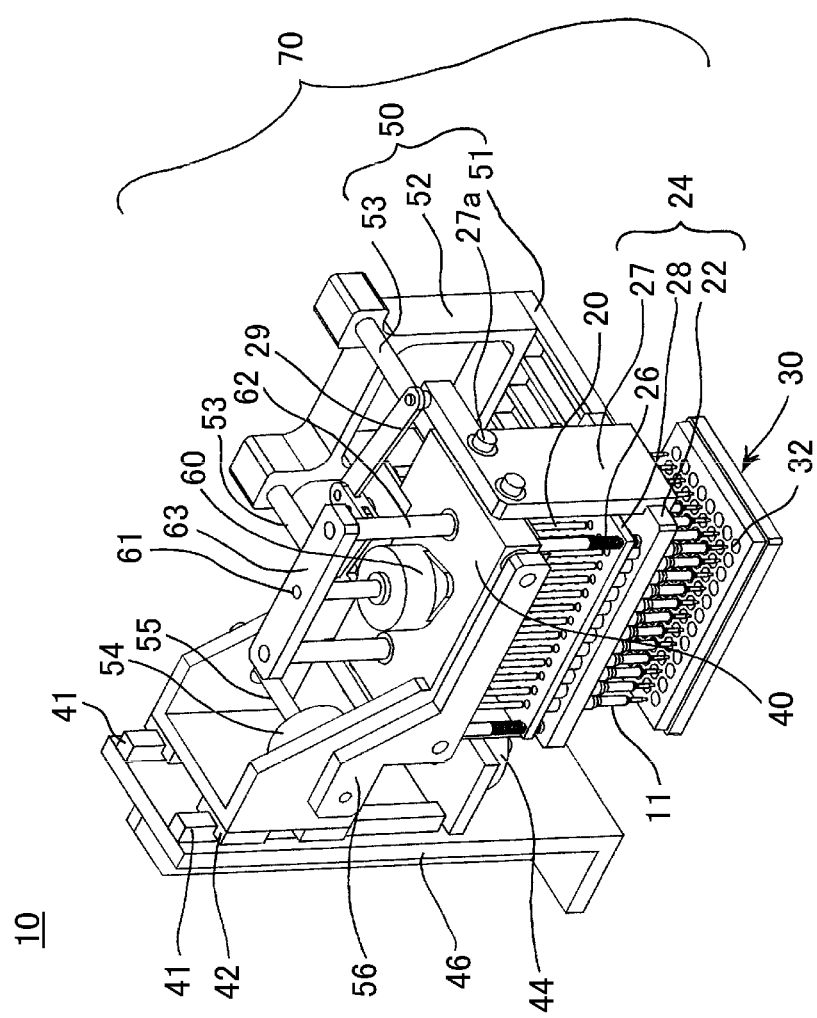

[Fig.5]
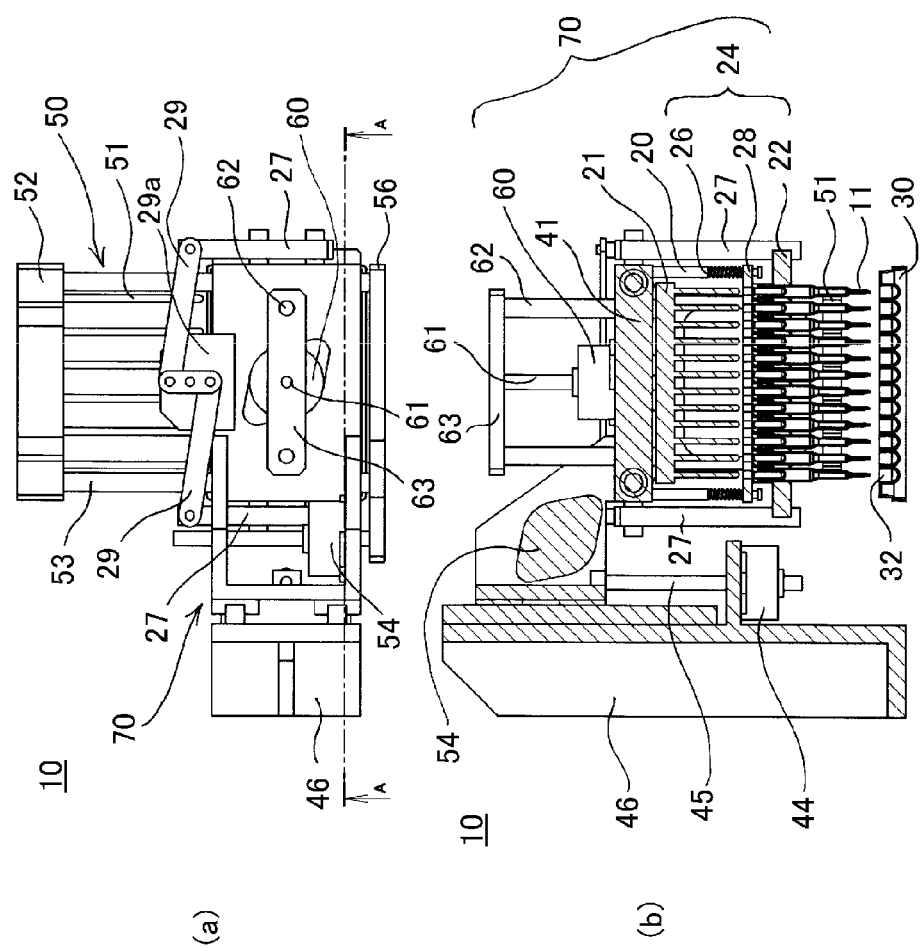

[Fig.6]
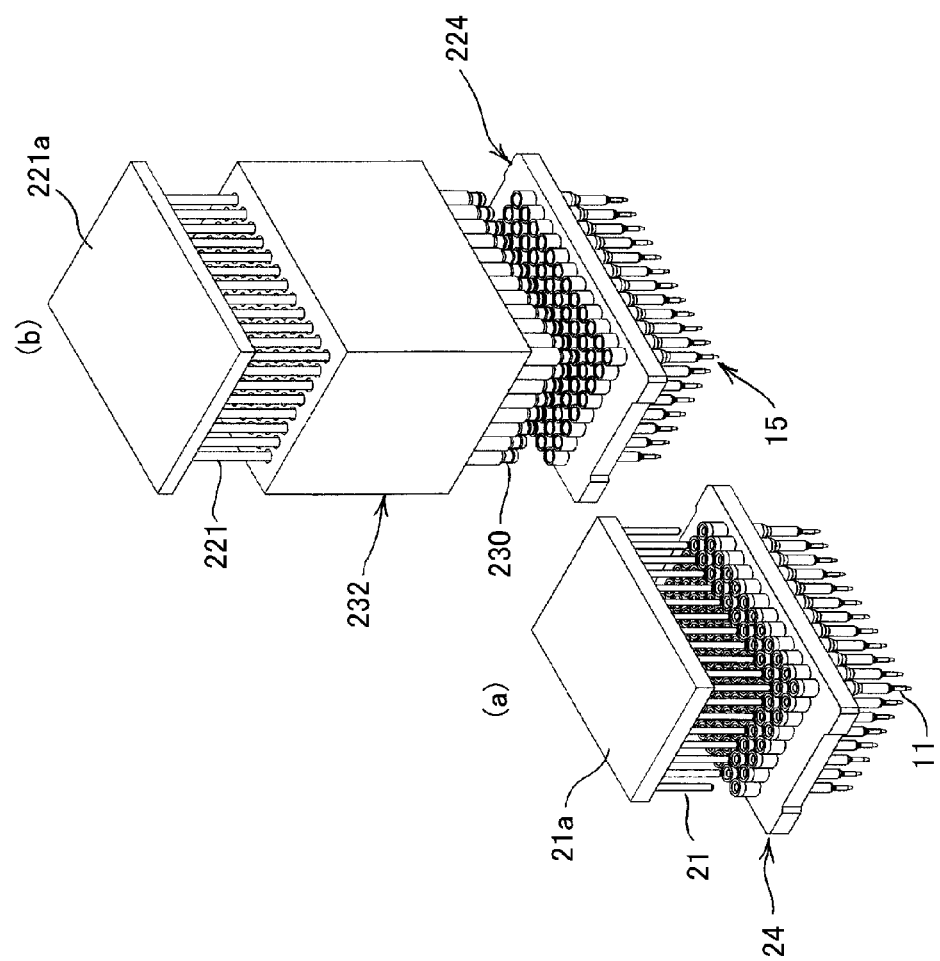

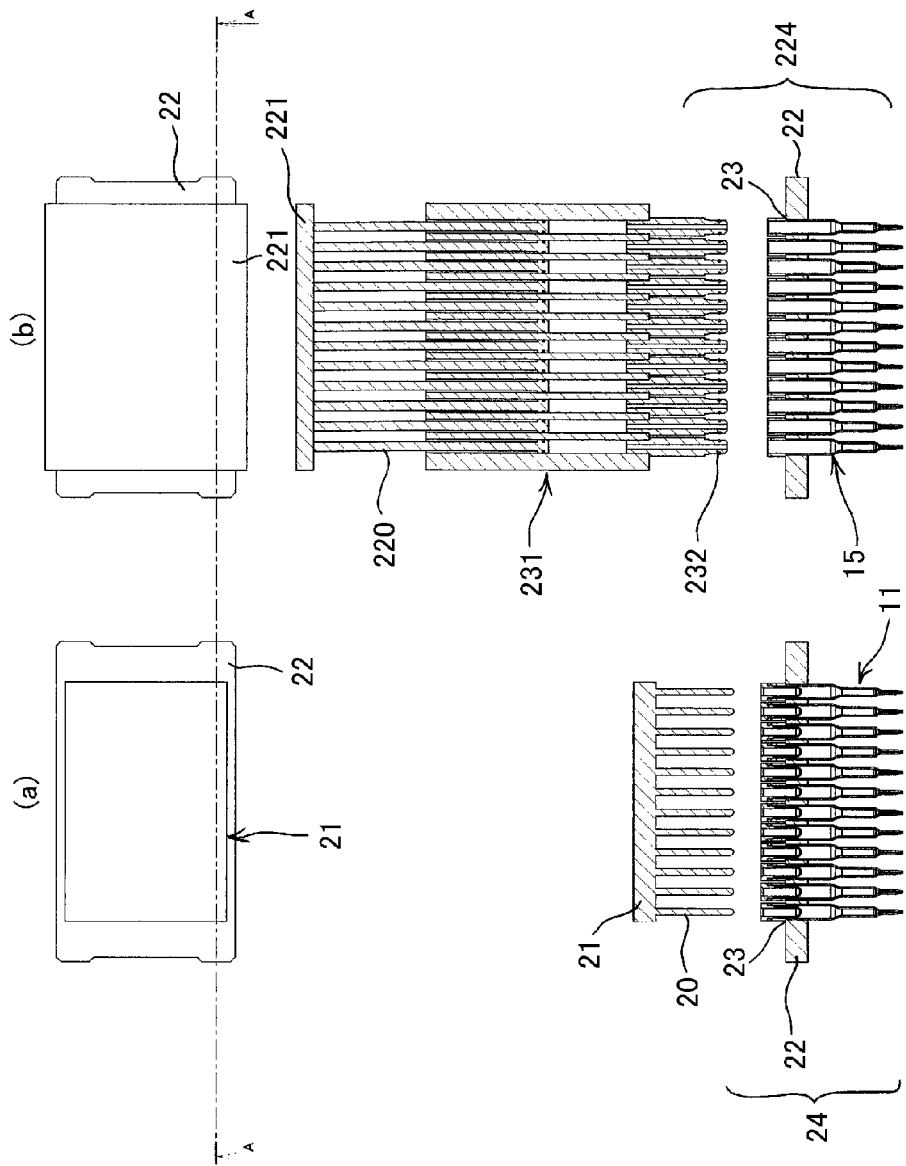
[Fig.7]

[Fig.8]
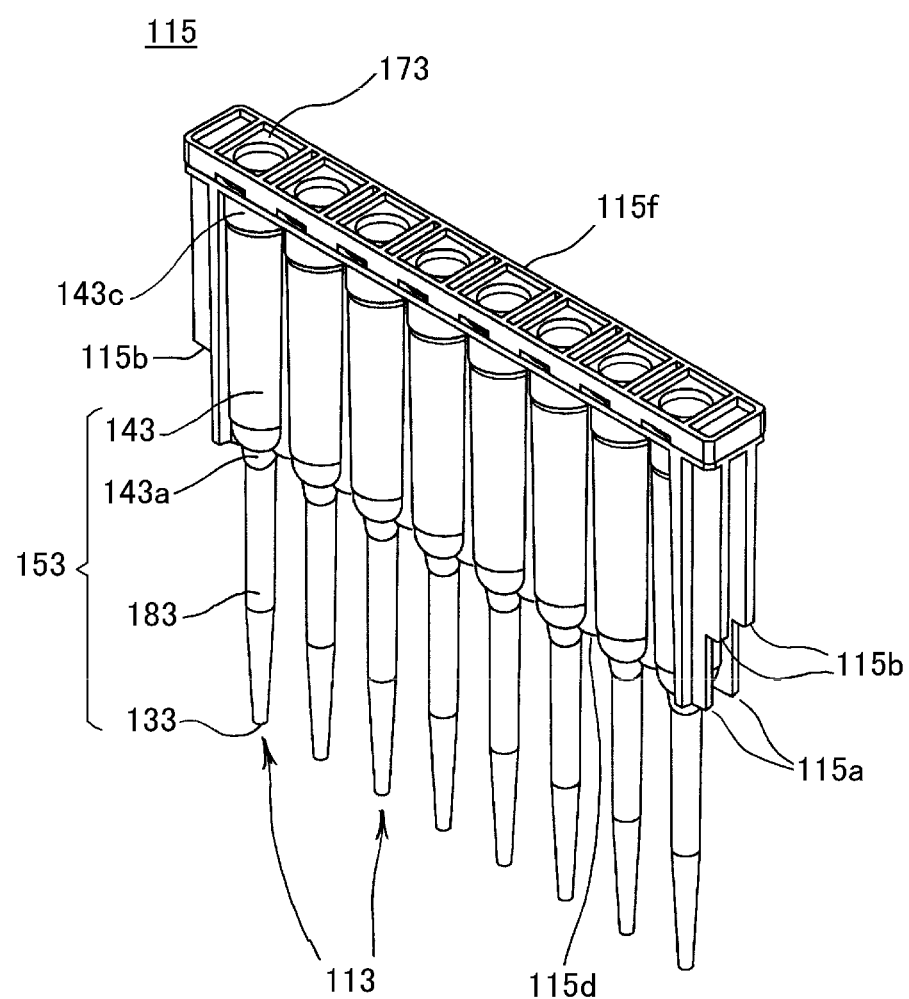

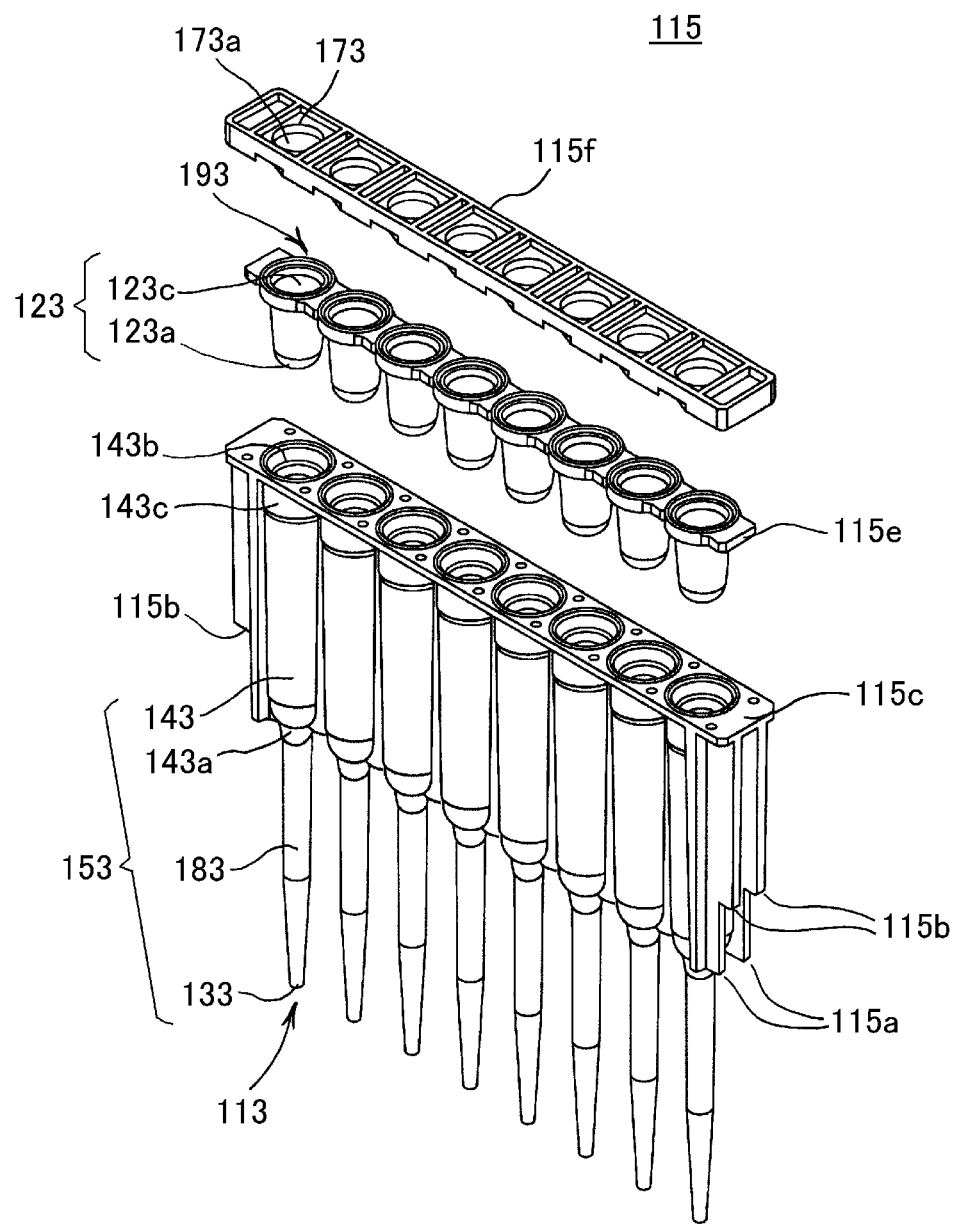
[Fig.9]

[Fig.10]
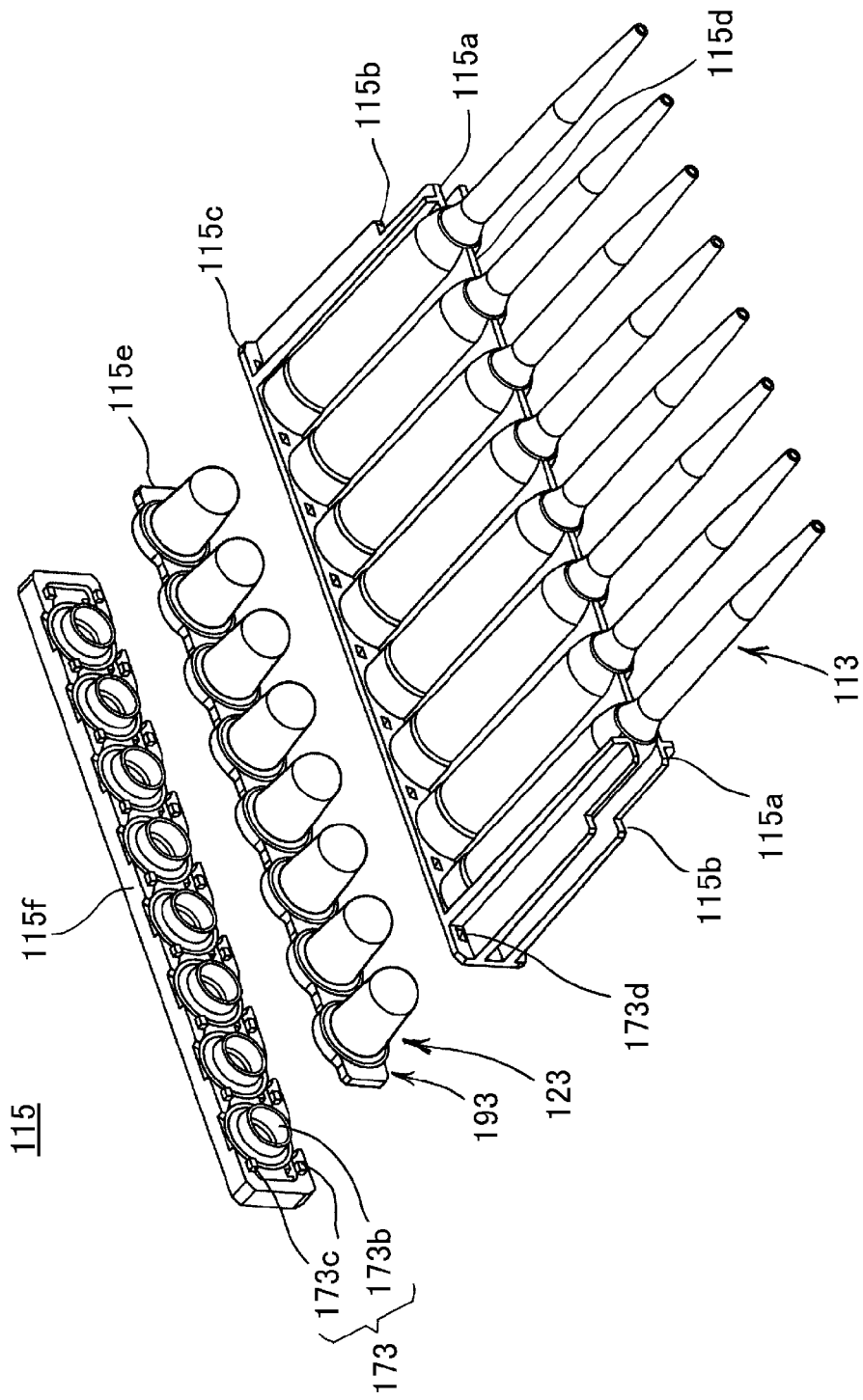

[Fig.11]
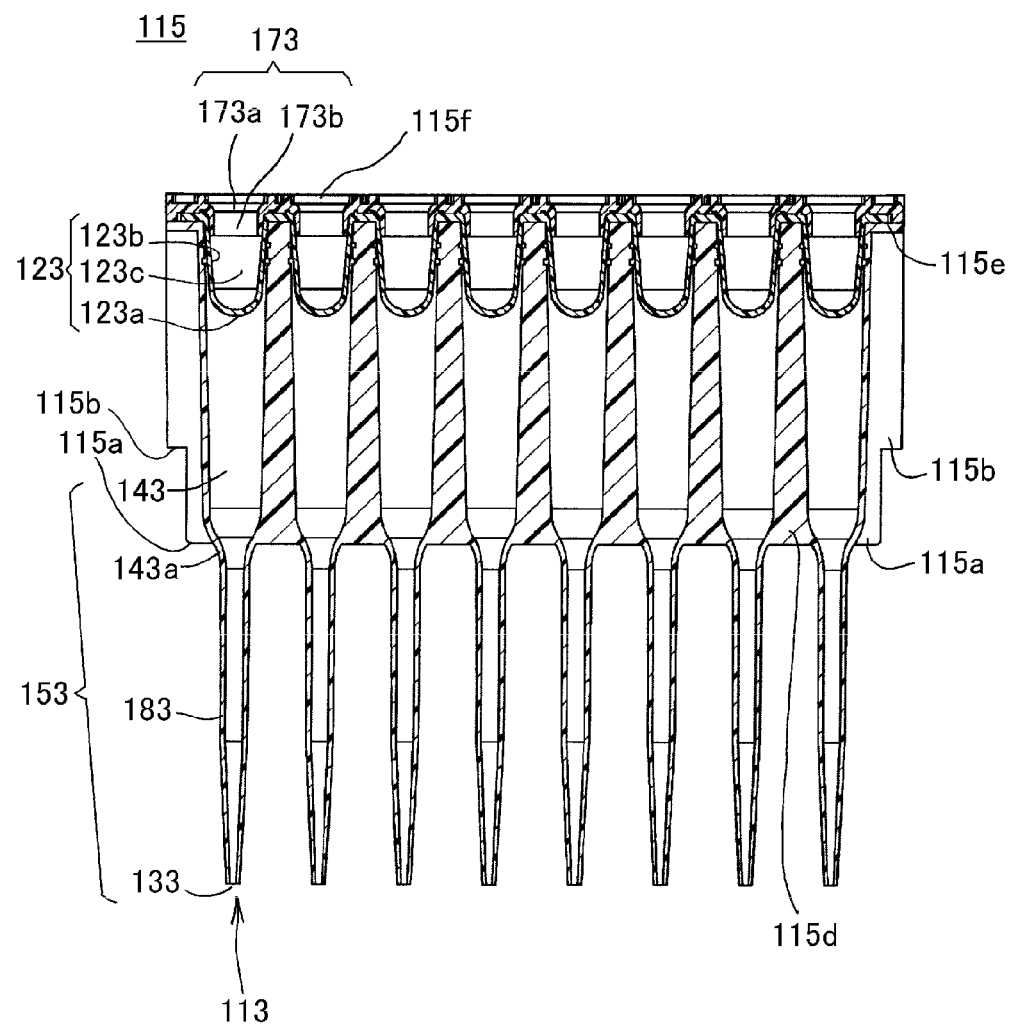

[Fig.12]
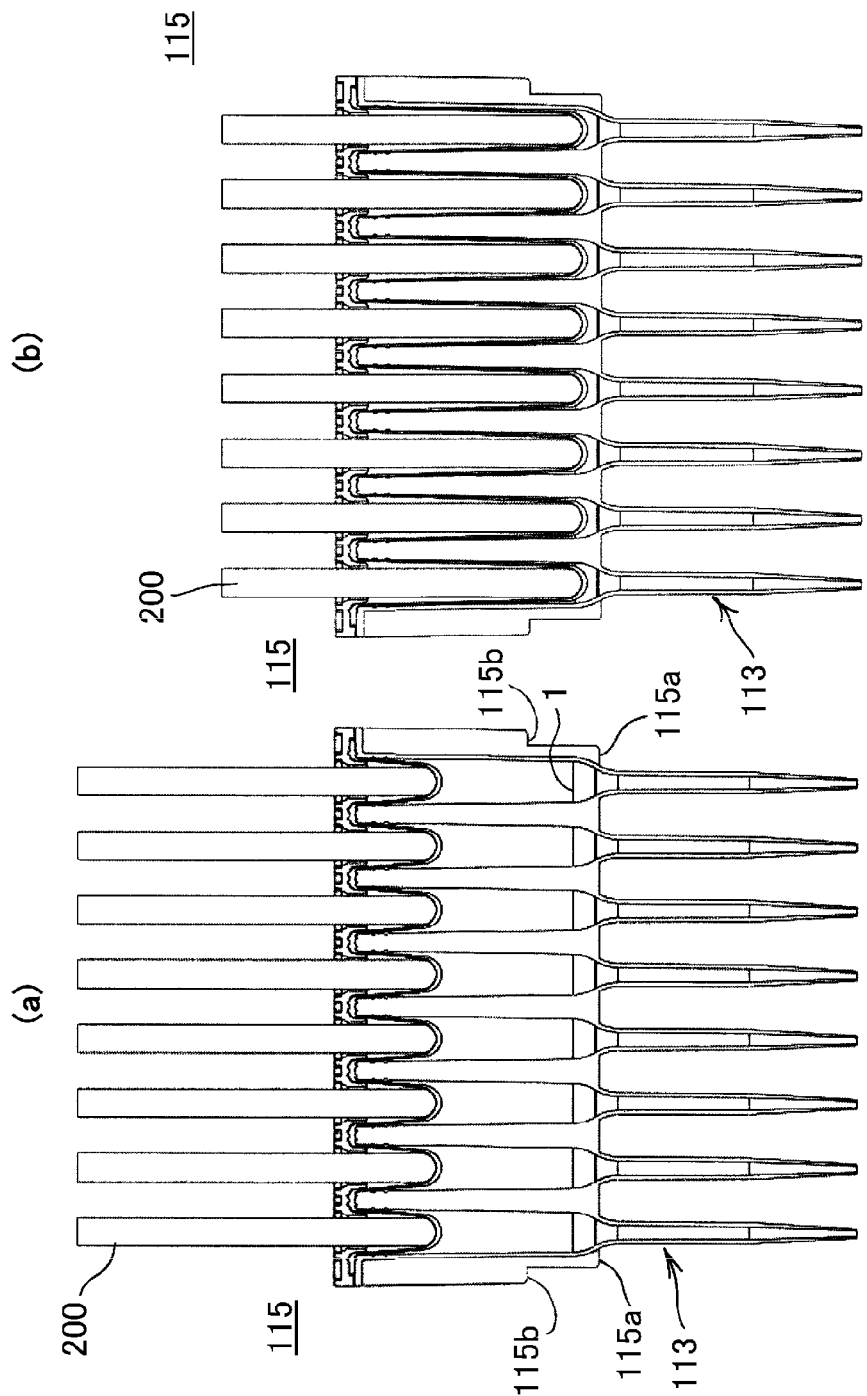

[Fig.13]
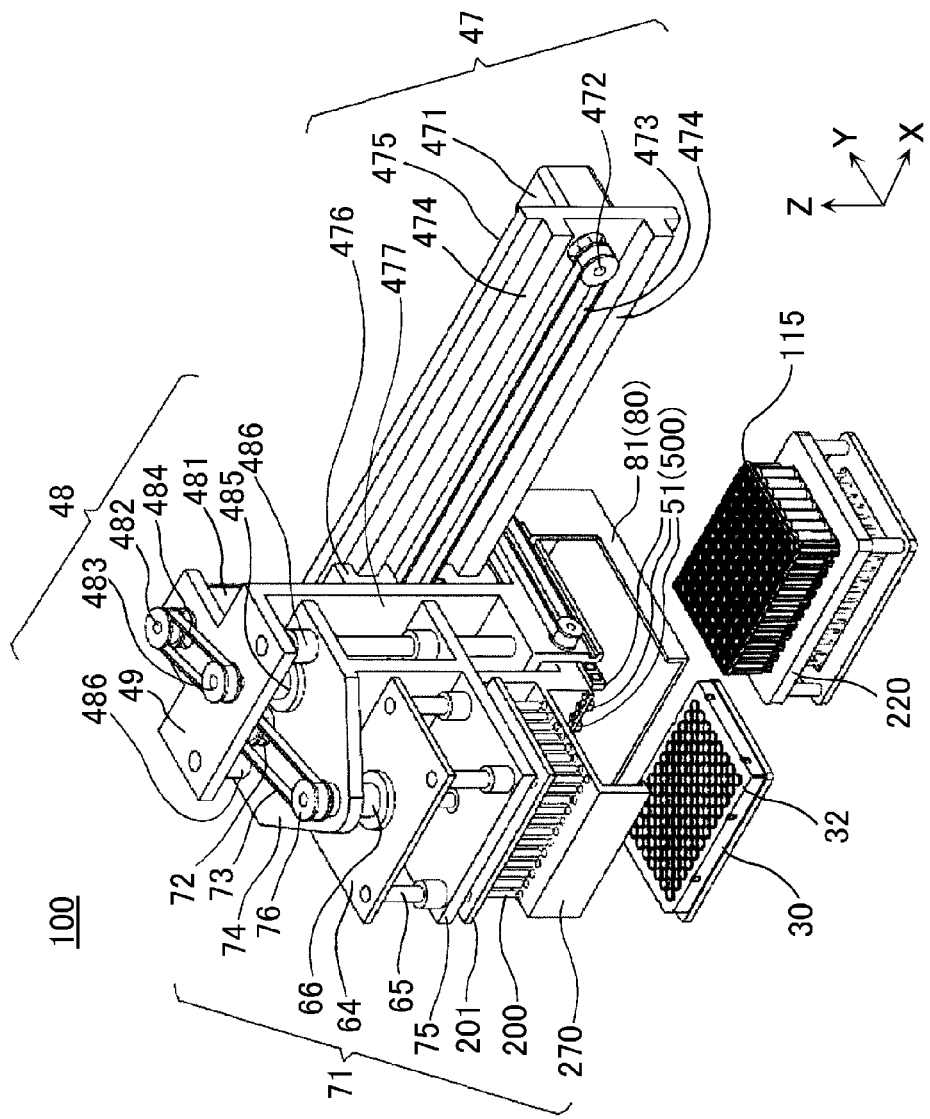

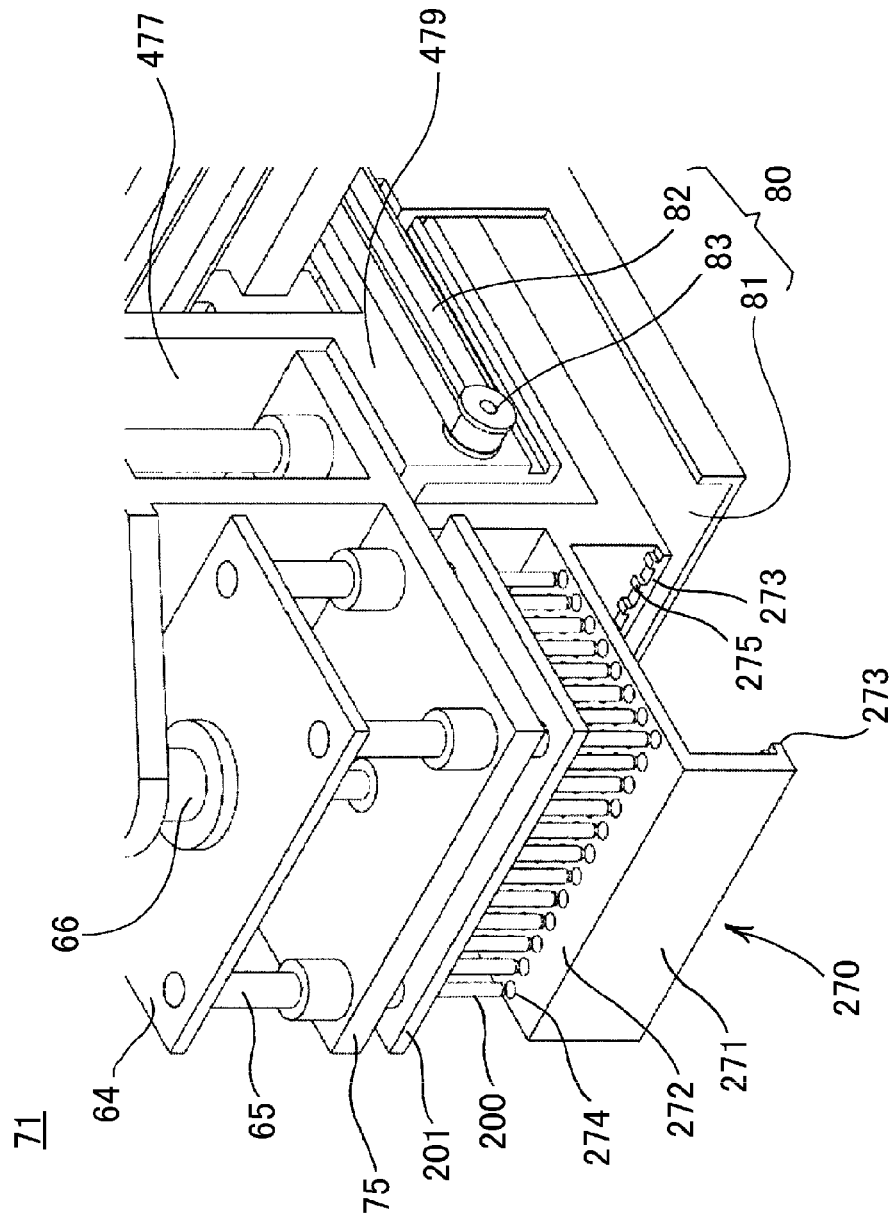
[Fig.14]

[Fig.15]
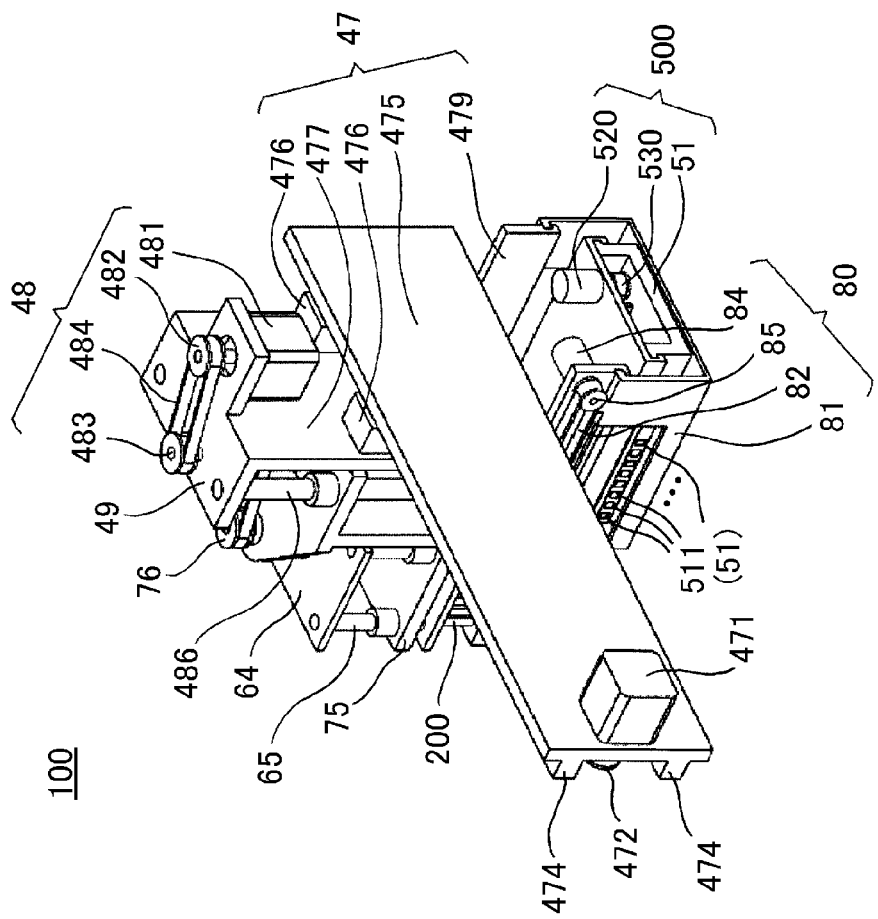

[Fig.16]
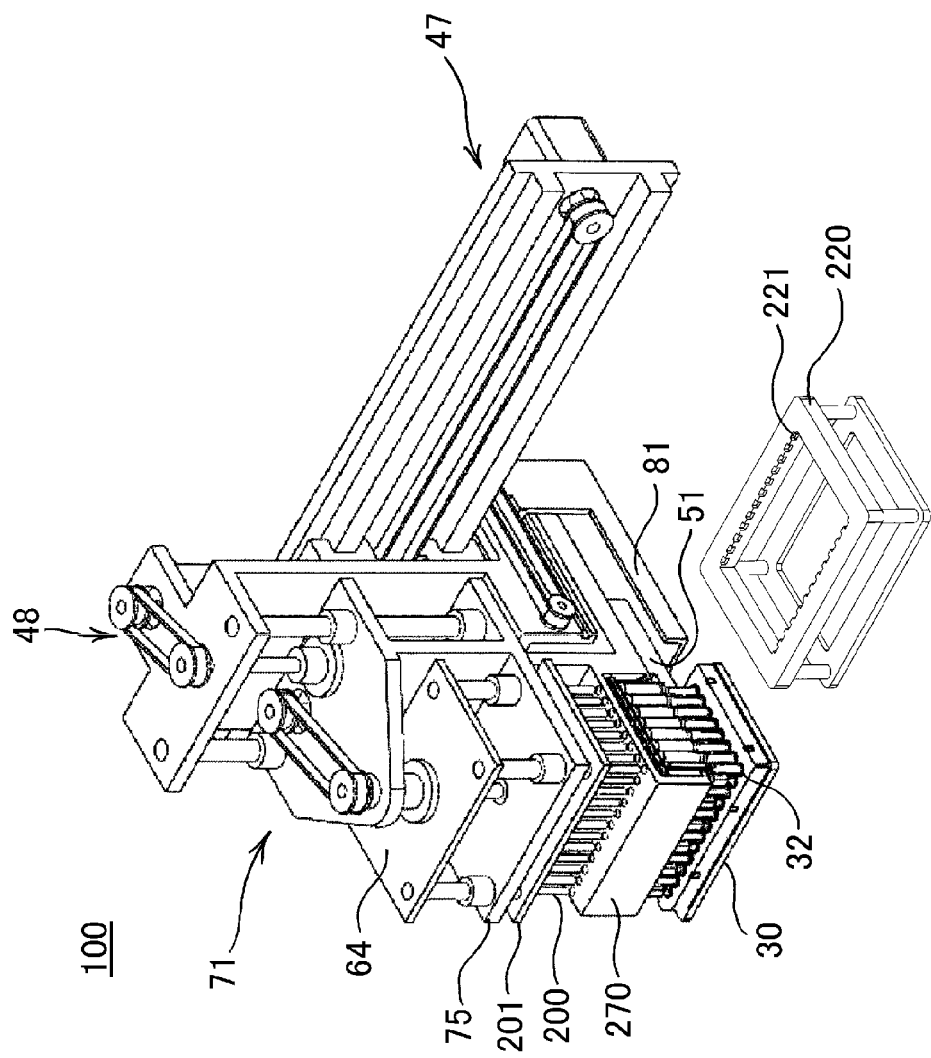

[Fig.17]
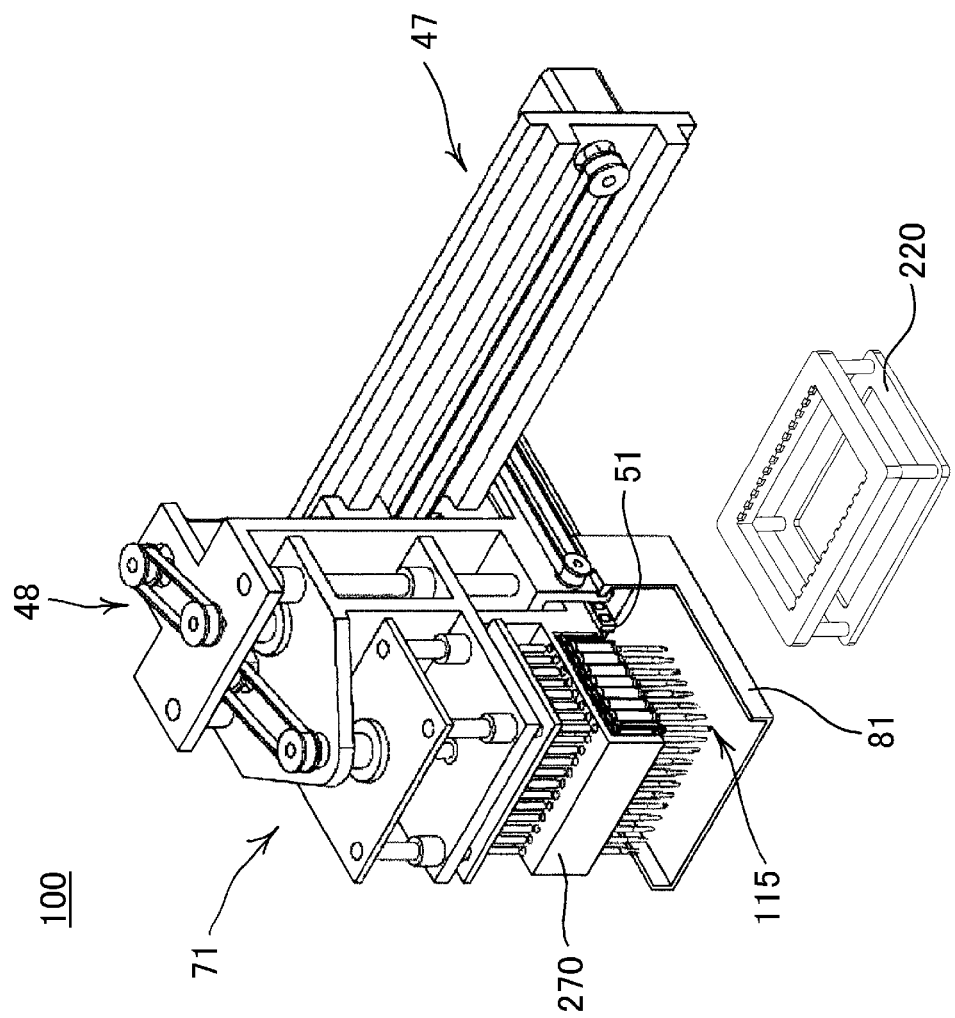

[Fig.18]
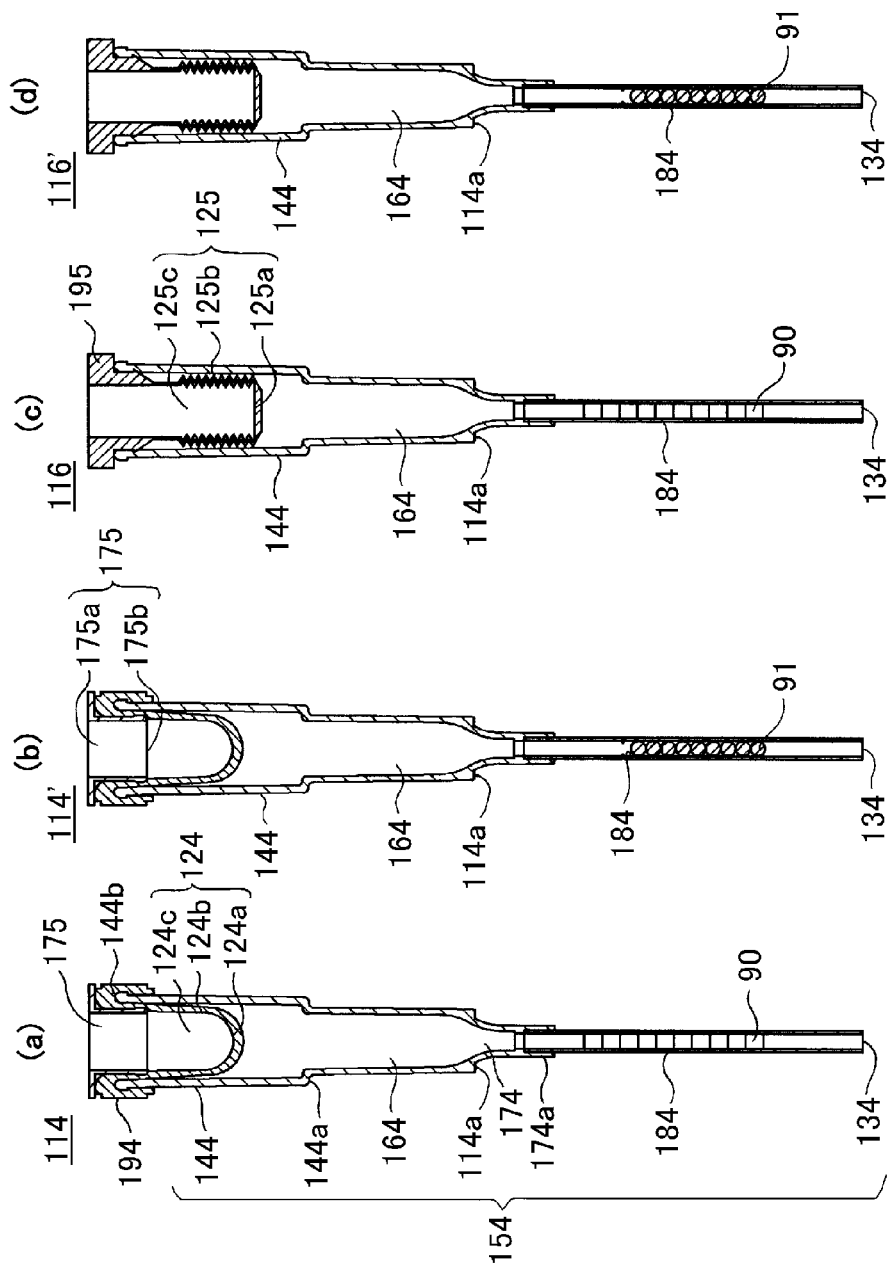

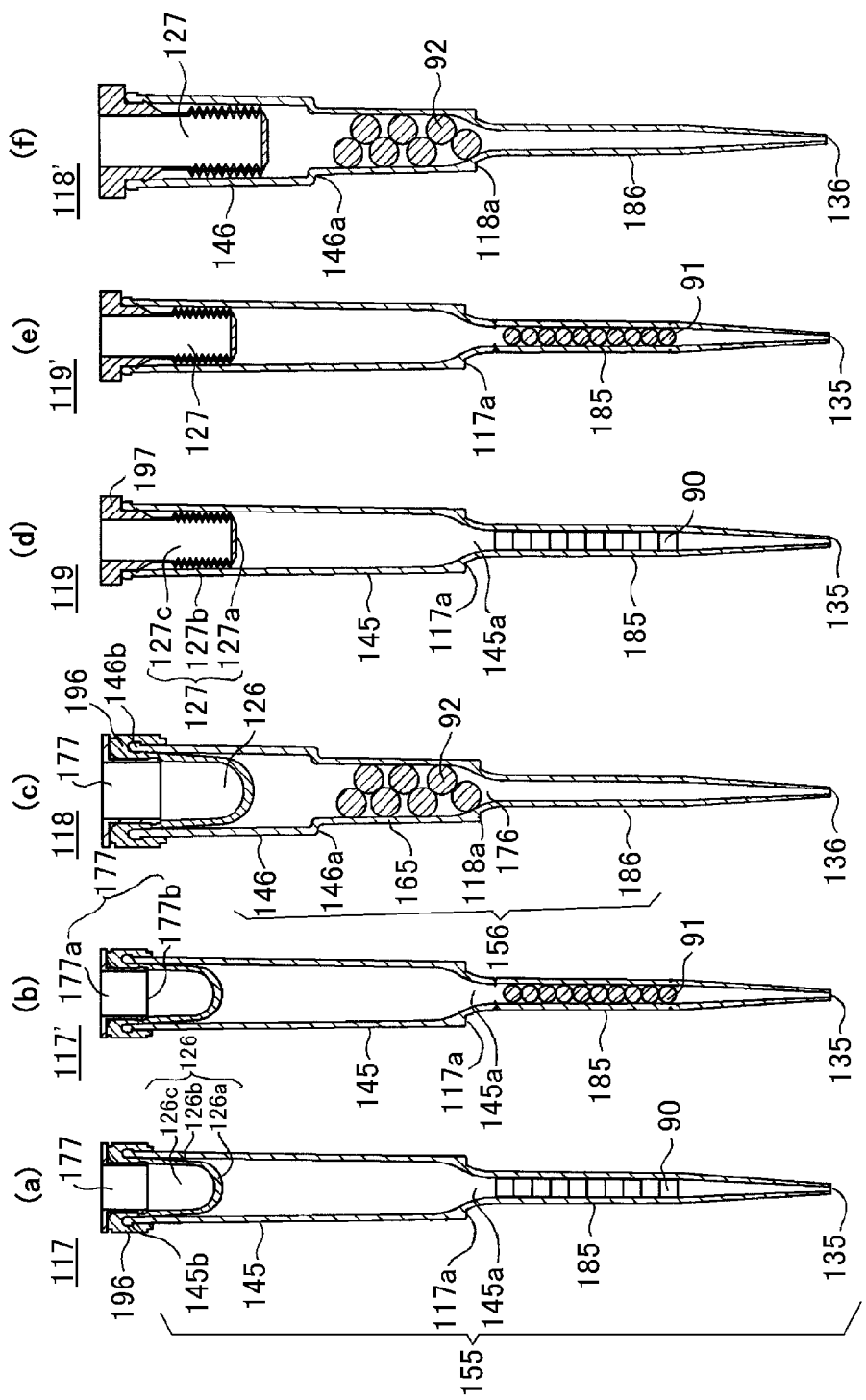
[Fig.19]

[Fig.20]
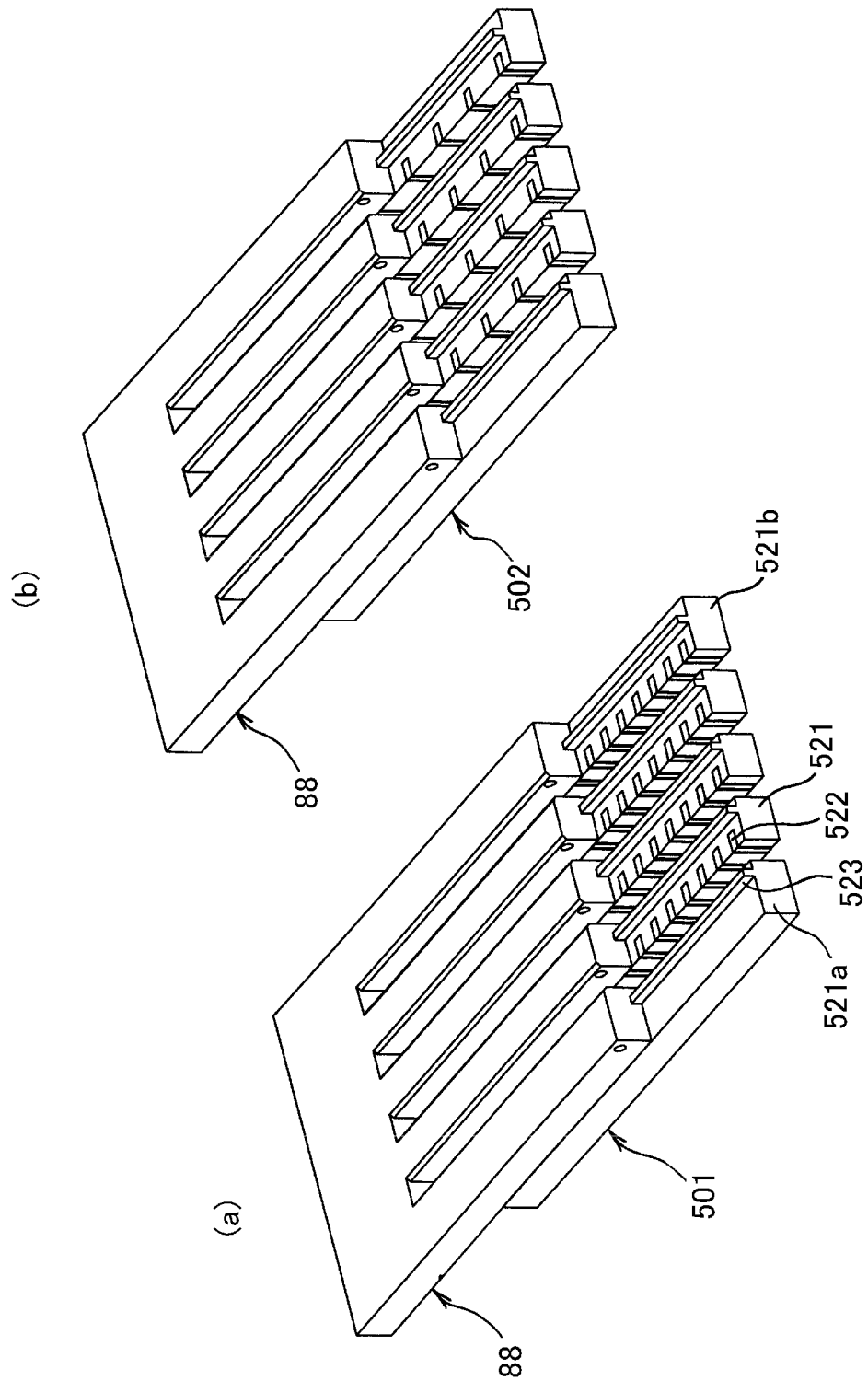

[Fig.21]
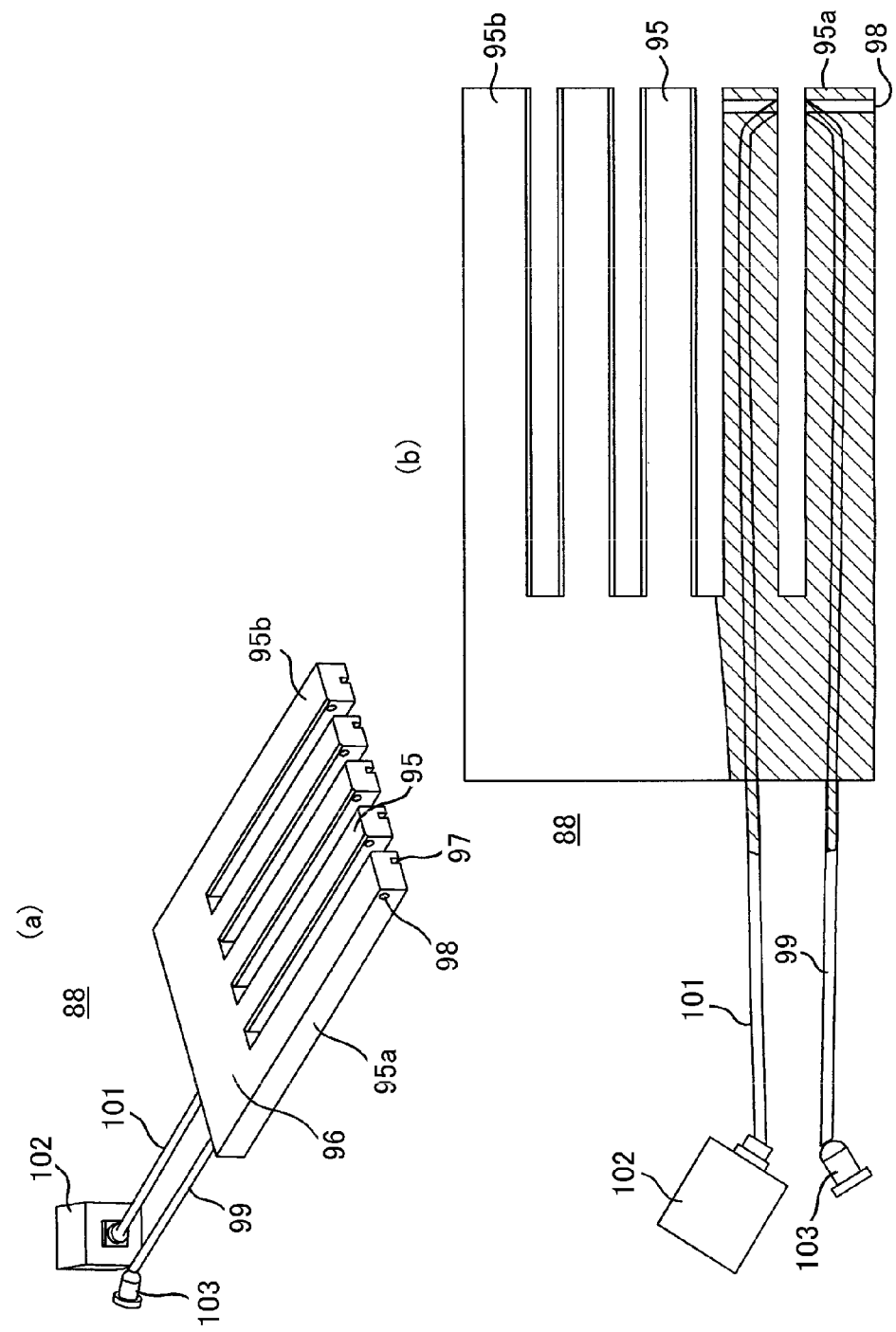

DEFORMING ELEMENT-INCLUDED DISPENSING TIP, DEFORMING ELEMENT-INCLUDED DISPENSING DEVICE, AND DEFORMING ELEMENT-INCLUDED DISPENSING PROCESSING METHOD

CROSS REFERENCE

This application is a United States national phase application of co-pending international patent application number PCT/JP2013/073513, filed Sep. 2, 2013, which claims priority to Japanese patent application number 2012-192519, filed Aug. 31, 2012 and Japanese patent application number 2013-126057, filed Jun. 14, 2013, the entire disclosures of which are hereby incorporated herein by reference.

TECHNICAL FIELD

The present invention relates to a deforming element-included dispensing tip, a deforming element-included dispensing device, and a deforming element-included dispensing processing method.

BACKGROUND ART

There is a dispensing device of which patent application was filed by the applicant of the present application and matured into a patent. In the dispensing device, a dispensing tip engages with and attaches to a lower end portion of a nozzle at an attachment opening portion, and a plunger in a cylinder in communication with the nozzle is caused to slide, so that a liquid is sucked or discharged through the lower end thereof into and out of the dispensing tip (Patent Literatures 1 to 4).

However, mechanisms such as a cylinder and a plunger used in the dispensing device are highly precisely processed components such as a syringe, and in particular, the change in the volume in the cylinder is basically integral with the change in the volume in the dispensing tip, and it is necessary to transmit it to a joint portion between the plunger and a driving device of the plunger without any looseness. The sucking and discharging mechanism thereof, the dispensing tip, and the like are engaged without any leakage of gas or liquid. For this reason, a high degree of quality control may be required. More specifically, in order to engage the nozzle of the sucking and discharging mechanism with the attachment opening portion of the dispensing tip without any leakage of fluid, a high load is imposed on the dispensing tip when the nozzle is attached because of the existence of an O ring and the like provided on the attachment opening portion, and, e.g., this may destroy the dispensing tip and may cause abrasion of the nozzle, and therefore, it is necessary to exchange the nozzle and processing with a high degree of accuracy. In order to control the sucking and discharging of the dispensing tip, a cylinder having a volume corresponding to the volume of the dispensing tip is necessary, and therefore, there is a problem in that the size of the device increases when a large volume of liquid is treated.

On the other hand, in the past, a pipette has been known, which is surrounded by a wall surface such as rubber and is capable of accommodating liquid and gas therein, wherein the pipette deforms when the wall surface is manually pressed, so that the pipette sucks and discharges liquid. However, since this pipette is manually handled, a single user can handle up to only a single pipette, and it is impossible to perform processing at a time using many pipettes. The deforming of the pipette is different according to the magnitude of the force, the direction of the force, and the position where the force is applied, and therefore, in the manual pipette operation, it is difficult to perform processing that is precise in terms of amount and perform repetition with a high degree of reproducibility.

As a method of improving this, the applicant of the present application has developed a device using a deforming-type dispensing tip in which a deforming wall surface forms a portion of a wall surface accommodating liquid and gas, and the device sucks and discharges liquid by deforming the deforming wall surface (WO 2007/081000). In the device using this deforming-type dispensing tip, gas is accommodated in an accommodation unit partially formed with the deforming wall surface that deforms, and therefore, it may be necessary to rigidity hold an inlet unit connected to an accommodation unit partially having the deforming wall surface so that it does not deviate.

Further, in order to deform the deforming-type dispensing tip as intended, it may be necessary to loosely insert the deforming-type dispensing tip into a holder and the like and use it so that the deforming wall surface deforms only in a predetermined direction.

The deforming wall surface is used for a portion of an external wall of the deforming-type dispensing tip, and there is a problem in that it may be deformed or damaged, and this may increase the burden in the quality control.

It should be noted that there is a method of directly transferring from a container to a container without using any dispensing tip. Although this method simplifies the device structure, a person is required, and there is a risk of contamination because of a contact between a container and a container, and there is a problem in that a high degree of reliability cannot be obtained.

CITATION LIST

Patent Literature

Patent Literature 1: JP 3115501 B1
Patent Literature 2: JP 3739953 B1
Patent Literature 3: JP 3630497 B1
Patent Literature 4: JP 3682302 B1
Patent Literature 5: WO 2007/081000 A

SUMMARY OF INVENTION

Technical Problem

Therefore, in order to solve the above problem, it is a first object of the present invention to provide a deforming element-included dispensing tip, a deforming element-included dispensing device, and a deforming element-included dispensing processing method having a simple and compact structure but still capable of handling several types of volumes (about several microliters to about several dozen milliliters) of liquids with a high degree of precision and capable of performing efficient processing. It is a second object to provide a deforming element-included dispensing tip, a deforming element-included dispensing device, and a deforming element-included dispensing processing method not requiring precision for watertightness, airtightness, and the like in production and quality control and capable of being provided at a low cost, and in addition, reducing the burden in management, and having no opening other than an inlet unit, and capable of reliably preventing cross contamination. It is a third object to provide a deforming element-included dispensing tip, a deforming element-included dispensing device, and a deforming-type dispensing processing method capable of consistently performing various kinds of complicated processing. It is a fourth object to provide a deforming element-included dispensing tip, a deforming element-included dispensing device, and a deforming element-included dispensing processing method capable of preventing the position of the dispensing tip from deviating due to deforming and still capable of controlling the position with a high degree of precision by including a deformable portion in the dispensing tip formed by a non-deforming wall without forming an external wall of the dispensing tip with a deformable deforming wall. It is a fifth object to provide a deforming element-included dispensing tip, a deforming element-included dispensing device, and a deforming element-included dispensing processing method capable of enabling the dispensing tip to be integrated with a high degree of density and having many advantages resulting from the integration by including a deformable portion in the dispensing tip formed by a non-deforming wall without forming an external wall of the dispensing tip with a deformable deforming wall. It is a sixth object to provide a deforming element-included dispensing tip, a deforming element-included dispensing device, and a deforming element-included dispensing processing method capable of reducing the load of quality control by including a deformable portion in the dispensing tip formed by a non-deforming wall without forming an external wall of the dispensing tip with a deformable deforming wall. Further, it is a seventh object to provide a deforming element-included dispensing tip, a deforming element-included dispensing device, and a deforming element-included dispensing processing method capable of efficiently, swiftly, and easily performing the processing such as handling and measurement of a carrier by sealing a carrier bonded with or capable of being bonded with various kinds of substances such as biological materials into a deformable container.

Solution to Problem

A first invention relates to a deforming element-included dispensing tip comprising: a tip-shaped container formed with a non-deforming wall having an opening portion at an upper side and an inlet unit at a lower side for allowing fluid to flow in and flow out; and a sealing plug attached to the opening portion so as to seal the opening portion, wherein the sealing plug is provided with a deforming element that has a deforming wall that is formed so as to be able to extend in a lower direction in the tip-shaped container in accordance with pressing from an outside and is formed so as to be urged to shrink or be able to shrink in an upper direction, and the deforming element is formed so as to be located inside the tip-shaped container.

In this case, "attachment" includes engagement, adhesion, thermal adhesion, ultrasonic adhesion, and welding. The sealing plug may be held with a hold-down plate and attached to an opening portion from above. Alternatively, it may be attached with an O ring interposed therebetween. The "deforming wall" means a flexible wall that can deform. An elastic wall is also included within the range of flexible wall. The "non-deforming wall" is a wall having such rigidity that the wall is neither deformed nor destroyed by an external force that can deform the deforming wall.

The deformation of the "deforming wall" is preferably deformation such that an internal volume is substantially determined in accordance with the degree of applied deformation. More specifically, it is preferable that the internal volume is uniformly determined by causing the inside surrounded by the wall to be expanded or shrunk in accordance the degree of pressing or pulling the deforming wall along any given deforming direction or removing the force.

Examples of deforming walls include a wall formed with bellows, or a wall including a spring and the like formed with an elastic member explained later or having an elastic force along a deforming direction.

In this case, the "bellows" means a planar member or a film member formed with waves or folds having peaks and valleys formed along a direction crossing a predetermined deforming direction in a substantially perpendicular direction, and that can bend at the peaks and valleys.

When the planar member or the film member formed with bellows is used for the wall surface enclosing in a tubular manner with the deforming direction being the axis, the shape of the wave or fold may be made of peaks and valleys in a straight manner perpendicular to the deforming direction, or a circumferential manner included in the plane perpendicular to the deforming direction, or in a closed curve manner (a curved line includes a straight line), or may be such that projections and depressions are formed to be inclined and formed in a spiral manner.

Examples of materials of the deforming element-included dispensing tip include resins such as polyethylene, polypropylene, polyester, polystyrene, polyvinyl, and acryl, and an elastic body such as rubber, and other flexible materials, or a combination thereof. The deforming element-included dispensing tip is preferably transparent or semi-transparent. Synthetic rubber, silicone, natural rubber, isoprene synthetic rubber, and the like are used as the deforming wall. For example, polyethylene, polypropylene, polystyrene, and the like are used as the non-deforming wall.

The size of the tip-shaped container of the deforming element dispensing tip is such that, for example, the length from the inlet unit to the opening portion or along the axis direction is several centimeters to several dozen centimeters, and the volume thereof is, for example, about several microliters to several dozen milliliters in accordance with the length thereof.

In this case, the tip-shaped container is preferably formed such that the axis line passing the inlet unit and opening portion is formed along the vertical direction. The tip-shaped container is formed with, for example, the resin, and as the deforming wall, for example, a sealing plug having the deforming element provided with bellows is formed with blow molding, and the tip-shaped container is formed with injection molding. Alternatively, all of them are formed with blow molding.

A second invention relates to a deforming element-included dispensing tip wherein the tip-shaped container comprises a deforming element containing portion having the opening portion and capable of receiving the deforming element so as to encompass a deformable range of the deforming element, and a narrow tube portion formed to be narrower than the deforming element containing portion and having the inlet unit.

In this case, the length of the "deformable range" from the sealing plug in the vertical direction is configured to be equal to or longer than the maximum extension distance of the deforming element.

An accumulation portion is preferably provided to be in communication with the deforming element containing portion and the narrow tube portion and capable of accumulating liquid sucked from the inlet unit, and gas is preferably stored in the deforming element containing portion, and sucking and discharging of the liquid is preferably controlled so that the liquid sucked to the narrow tube portion and accumulation portion is accommodated therein. Therefore, the liquid does not contact with the deforming element, the liquid does not penetrate into and remain in the space sandwiched between the deforming element and the inner wall of the deforming element containing portion, and the liquid does not remain in the folds of the bellows of the deforming element, so that a high degree of property in the constant amount can be ensured.

Alternatively, without separately providing an accumulation portion, both of gas and liquid are allowed to be accommodated in the deforming element containing portion, and in a state in which the deforming element is not extended, in a minimum extension state, or in a shrunk state, liquid may be accommodated up to a position where there is no contact with the deforming element in the deforming element containing portion.

By forming the distal end of the narrow tube portion in a tapered shape or a sharp shape, insertion into various containers is permitted, and the sucking and discharging are simplified, and for a prepack type accommodation container of reagent and the like made by accommodating a solution including reagent, sample, or the like in advance and covering the opening portion thereof with a film, the film is stubbed by the narrow tube portion, so that the solution accommodated in the container can be sucked through the narrow tube portion.

A third invention relates to the deforming element-included dispensing tip, wherein the sealing plug has a depression surrounded by a tubular wall projecting to an inside of the tip-shaped container as the deforming element, and the tubular wall comprises a bottom wall on which force is exerted from an outside to extend the deforming element, and a side wall having the deforming wall.

The tubular wall comprises the bottom wall and the side wall, and the bottom wall is formed so as to be able to be in contact with or connected with a device for deforming the deforming element, and more specifically, the bottom wall is formed so as to be able to be in contact with or connected with a pin which is a movable member explained later. At least a portion of the side wall is formed with the deforming wall. It is preferable to be accommodated in such a state that the side wall of the deforming element and the inner wall of the deforming element containing portion are in proximity to each other. Therefore, the deforming element can most greatly change the volume of the deforming element containing portion.

A fourth invention relates to the deforming element-included dispensing tip, comprises a hold-down plate attached to the tip-shaped container at the upper side of the sealing plug and holding the sealing plug from the upper side, and the hold-down plate is provided with an operation hole, and a protection wall formed so as to extend in the lower direction from the peripheral portion of the operation hole so as to be surrounded by the deforming element.

The hold-down plate is formed with the non-deforming wall. The operation hole needs to be provided to allow contact or connection from the outside to the deforming element through the hole. For example, a movable member comes into contact with or connects with the deforming element. The protection wall is to prevent the deforming wall covered with the protection wall from being contacted from the outside, and for example, the protection wall prevents contact between the deforming element and the movable member inserted from the operation hole, and allows smooth operation by removing abrasion and resistance applied to the movable member, and in addition, for the deforming element, attachment to the tip-shaped container is enforced, and abrasion and wear with the movable member are avoided, so that the degradation of the deforming element can be delayed.

When the sealing plug has a depression, the protection wall extends in the lower direction in the depression, and a portion of the tubular wall is covered with the protection wall.

A fifth invention relates to the deforming element-included dispensing tip, wherein the sidewall comprises a flexible member, and is formed with bellows.

A sixth invention relates to the deforming element-included dispensing tip, wherein the side wall has an elastic member.

A seventh invention relates to the deforming element-included dispensing tip, wherein the sealing plug has an elastic member, and is attached to the opening portion of the tip-shaped container by using an O ring.

In this case, even if the sealing plug is attached to the tip-shaped container without using adhesion nor welding, watertightness and airtightness can be maintained. Therefore, the sealing plug can be detachably attached to the tip-shaped container.

An eighth invention relates to a deforming element-included dispensing tip in which a carrier bonded with or capable of being bonded with a predetermined substance is enclosed in the tip-shaped container in a state of capable of coming into contact with a fluid that flows in and out through the inlet unit.

In this case, the area where the carrier is enclosed is preferably "an area where the inside can be measured from the outside", and surrounded by the non-deforming wall having translucency, and in that area, the carrier is preferably enclosed in such a state that it is not in contact with the deforming element. The "enclosing" means that something that is accommodated in the container having the inlet through which the fluid can flow in and flow out (for example, carrier) is held so that it does not flow outside of the container through the inlet unit. During measurement, instead of allowing the carrier to freely move in the tip-shaped container, the carriers are preferably in a substantially stationary state and movable from each other or with respect to an introduced liquid. However, the carrier is not necessarily completely fixed. In order to enclose the carrier, an enclosing portion may be provided. The "enclosing portion" is a portion where the fluid can pass through but the carrier cannot pass through in a case where the inlet unit has such a size that allows the carrier to pass through. The enclosing portion is made discretely from the non-deforming wall of the tip-shaped container or processing the non-deforming wall and is provided so as to separate the tip-shaped container across the flow direction of the fluid. The case where the enclosing portion is discretely provided includes a case where it is attached to the non-deforming wall and a case where it is not attached thereto. The case where is made by processing includes a case where it is swaged. Shapes of the enclosing portion s include members provided so as to separate a thin tube in a wheel shape, a cross shape, a straight line, a radial line, a mesh form, or a circular form, and a penetrating porous member having penetration holes. The flow direction of the fluid may be in a thin plate shape or a thin membrane manner. At least one enclosing portion is provided in order to prevent the carrier from flowing out from the inlet unit.

A solid object that can be bonded with a predetermined substance or capable of being bonded with a predetermined substance is made of, for example, resins holding a porous substance, resins holding a predetermined functional group or a predetermined chemical compound, organic substances including natural products such as fibroid substance, inorganic materials such as metal, semiconductor, glass, and silica. Examples of shapes of the carriers include a particle shape, a line shape, a stick shape, a planer shape, a block shape, and the like. It should be noted that the "predetermined substance" includes biological chemical compounds such as genetic substances such as oligonucleotide and nucleic acid such as DNA and RNA, various kinds of chemical compounds such as proteins such as immunity substances, peptides, amino acids, sugars, sugar chains, and the like, or living bodies themselves or living tissues such as cells, bacteria, virus, and plasmid. The "predetermined substance" is not limited to a case where it is only one type, and includes a case where there are multiple types of substances. The biological chemical compound is used to, e.g., detect bonding of, capture, separate or extract, a biological chemical compound serving as an acceptor having a bonding property with the biological chemical compound serving as a ligand. The acceptor corresponds to biological materials such as genetic substances such as nucleic acid, protein, sugar chain, peptide, and the like having bonding properties with genetic substance such as the nucleic acid, sugar chain, peptide, and the like. Instead of the biological chemical compounds, living bodies themselves such as cells, virus, plasmid, and the like can also be used. The carrier has a predetermined substance, e.g., a bonding body with a ligand or an acceptor, or is fixed with a substance considered to have a bonding property, for example, either an acceptor or a ligand.

The "bonding" means associating, with the carrier, at least one type of predetermined substance directly or via another type of substance. Examples of bonding include not only those based on covalent bonding and chemical adsorption but also those based on physical adsorption, hydrogen bonding, electrical interaction, and the like. A predetermined chemical substance is fixed to the carrier by chemical adsorption or physical adsorption, or is bonded by a special reaction with a bonding substance provided fixedly to the carrier, or other methods. Alternatively, when the carrier is formed with a porous member, an uneven member, and a fiber member, the reaction performance or the bonding performance with a biological material and the like may be enhanced.

Examples of materials of "carriers" include inorganic substances such as ceramics, glass, silica, metal, semiconductor, semimetal, metal chemical compounds such as oxidized metal, and the like, and organic substances such as macromolecular substances such as rubber, latex, polystyrene, polypropylene, polyester, resin such as acryl, cellulose, fiber substances such as nylon explained above, and natural substances such as natural fibers such as silk. More specifically, for example, when a fiber substance is used as an example, the carriers are silk and the like, nylon (3-nylon, 6-nylon, 6,6-nylon, 6,10-nylon, 7-nylon, 12-nylon and the like) made of "polyamide-based polymers", wholly aromatic polyester such as PPTA (Poly-p-phenylene terephthalamide), heterocyclic ring aromatic polymer, and the like. Alternatively, for example, fibrous bodies, porous bodies, and gel-like bodies may be used as the carriers.

For bonding, the carrier expresses or generates a functional group. Therefore, for example, peptide bonds of the "polyamide-based polymers" are hydrolyzed, so that the functional group used for the bonding of the biological material is expressed or generated. Examples of functional groups that can be bonded with the biological materials include carboxyl group-COOH, amino group-NH2, and inductions thereof. The diameters of the holes of the porous material suitable for bonding of the biological chemical compounds are, for example, equal to or less than several micrometers.

The "carrier" is a solid of such a size that can be enclosed in the carrier-enclosed deforming container and in which the position that is bonded or the position can be bonded with the predetermined substance can be identified from the outside of the carrier-enclosed deforming container. With the carrier, the position that is bonded or the position that can be bonded is associated with a predetermined position of a carrier with an interval therebetween so that the predetermined substance is bonded or can be bonded, or in association with multiple predetermined carriers, the carrier is preferably enclosed in the carrier, so that, for example, the position that is bonded or the position that can be bonded can be identified for example, with a one dimensional coordinate along the axis direction of the carrier-enclosed deforming container or in a random state. Examples of such carriers include one or more particle-like carriers, cubic carriers, line-like carriers, stick-line carriers, strip-shaped carriers, flat plate-like carriers, block-like carriers, and the like.

In this case, a solution including a predetermined substance labelled with a labelling substance made of a light emitting substance such as a fluorescence substance that may be bonded with the carrier itself or a substance fixed to the carrier is brought into contact with the carrier in the tip-shaped container, so that the presence/absence of the bonding with the biological material is measured by measuring the light emission at each position, and therefore, the structure, the property, and presence/absence of the object biological material can be analyzed.

The size of the deforming container is, e.g., a length between crossing points between the deforming wall surface and the inlet unit along the line passing through the inlet unit and surrounded by the accommodation unit, or the length in the axis direction is several centimeters to several dozen centimeters, and the volume thereof is about several microliters to several dozen milliliters in accordance with the length thereof.

It should be noted that the carrier may be a set of multiple particle-like carriers or multiple particle-like carriers that are bonded with or that can be bonded with multiple types of chemical substances and can be distinguished from the outside. In this case, the "particle-like carrier" is a particle-like solid having a size that can be introduced and held in a portion of the tip-shaped container where the carrier is enclosed. Normally, a single particle-like carrier or a set of particle-like carriers correspond to a single type of multiple types of chemical substances that are bonded or that can be bonded therewith. The size of the particle-like carrier is such that, for example, the diameter or the distance across is 0.1 mm to several mm. In the spatial portion where the particle-like carriers are enclosed, the volume thereof is such that the spatial portion except the enclosed particle-like carriers is a volume of, for example, several microliters to several hundred microliters. A particle-like carrier or a set of particle-like carriers are labelled in accordance with the chemical substance that is bonded or that can be bonded, and therefore, it is not necessary to distinguish them in accordance with the arranged positions of the enclosed particle-like carrier or the set thereof.

A ninth invention relates to a deforming element-included dispensing tip cartridge comprising a plurality of tip-shaped containers formed with a non-deforming wall so as to be integrally coupled and provided with a plurality of opening portions at an upper side and provided with a plurality of inlet units at a lower side for allowing fluid to flow in and flow out, and a plurality of sealing plugs attached to the opening portions so as to seal the opening portions, wherein the sealing plug is provided with a deforming element that has a deforming wall that is formed so as to be able to extend in a lower direction in each of the tip-shaped containers in accordance with pressing from an outside and that is formed so as to be urged to shrink or so as to be able to shrink in an upper direction, and the deforming element is formed so as to be located inside each of the tip-shaped containers.

In each deforming element-included dispensing tip, the tip-shaped container is formed with the non-deforming wall, and the deforming element is included in the tip-shaped container. Hence, multiple deforming element-included dispensing tips can be easily integrated into a higher density by integrally forming a portion of the external wall of the tip-shaped container. In regard to the arrangement of the tip-shaped containers, they are arranged with a predetermined interval in a line or a planar manner (including a matrix form).

A tenth invention relates to the deforming element-included dispensing tip cartridge wherein each of the tip-shaped containers comprises a deforming element containing portion having the opening portion and capable of receiving the deforming element so as to encompass a deformable range of the deforming element, and a narrow tube portion formed so as to be narrower than the deforming element containing portion and having the inlet unit.

In some cases the liquid sucked from the inlet unit according to the deformation of the deforming element is sucked to the narrow tube portion. In other cases, a portion of the liquid may be accommodated into the deforming element containing portion. In the latter cases, it is preferable that the deforming element and the deforming element containing portion are formed so that the liquid does not come into contact with the deforming element, or that such amount is controlled to be preferably sucked. In this case, the magnetic field is given to the narrow tube portion. When the accumulation portion is provided and is in communication with the deforming element containing portion and the narrow tube portion and is capable of accumulating the liquid sucked from the narrow tube portion, it is preferable that the deforming element containing portions are integrally formed with each other. But the magnetic field can be given to the accumulation portion, and the narrow tube portion can be inserted into each container, and accordingly, the accumulation portions and narrow portions are preferably provided with gaps, respectively.

An eleventh invention relates to the deforming element-included dispensing tip cartridge, wherein the sealing plug has a depression surrounded by a tubular wall projecting to an inside of the tip-shaped container as the deforming element, and the tubular wall comprises a bottom wall on which force is exerted from an outside to extend the deforming element, and a side wall having at least the deforming wall.

In this case, each of the sealing plugs may be attached to the tip-shaped container, or multiple sealing plugs which are adjacent to each other and which are to be attached to multiple tip-shaped containers may be coupled with each other, and a line-like coupled sealing plug column may be formed.

A twelfth invention relates to the deforming element-included dispensing tip cartridge comprises a hold-down plate attached to the tip-shaped containers at the upper side of the sealing plugs and holding the sealing plugs from the upper side, and the hold-down plate is provided with an operation hole in association with each of the sealing plugs, and a protection wall formed so as to extend in the lower direction from the peripheral portion of the operation hole and so as to be surrounded by the deforming element.

In this case, the hold-down plate is formed with the non-deforming wall, and may be attached to each tip-shaped container, or a coupled hold-down plate made by coupling multiple hold-down plates may be formed.

A thirteenth invention relates to the deforming element-included dispensing tip cartridge, wherein the deforming element-included dispensing tip cartridge is provided with two engagement units which are a first engagement unit and a second engagement unit which are provided in a projecting manner or in a recessed manner with respect to an external direction at both ends along the arrangement direction thereof, and the first engagement unit is disposed at a first height, and the second engagement unit is disposed at a second height lower than the first height.

In this case, the first height and the second height are heights measured from the inlet unit, and the first height is preferably included within the height range of the deforming element containing portion.

The first engagement unit is used to provide support so as to cover the upper side of the deforming element-included dispensing tip cartridge like the suspension unit of the dispensing head, and the second engagement unit is used to give support to cover the lower side of the cartridge like the case of loading to the rack. Therefore, a transition from one of the supports to the other of the supports can be performed smoothly by just moving the cartridge using the dispensing head. An example of engagement unit is preferably, for example, a projection portion or a depressed portion with respect to the external direction formed with the non-deforming wall and provided to be able to provide support with not a single point but with approximately an external diameter from the deforming element containing portion to narrow tube portion at the first or second height with respect to the thickness direction of the cartridge in order to ensure stability for support. The "arrangement direction" is a row direction or a column direction when arranged in a matrix form.

A fourteenth invention relates to the deforming element-included dispensing tip cartridge, wherein in a state of capable of coming into contact with a fluid that flows in and out through the inlet unit, a carrier bonded with or capable of being bonded with a predetermined substance is enclosed in an area which is inside of the tip-shaped container and where the inside can be measured from the outside.

A fifteenth invention relates to a deforming element-included dispensing device comprising, one or more deforming element-included dispensing tips that has, a tip-shaped container formed with a non-deforming wall having an opening portion at an upper side and an inlet unit at a lower side for allowing fluid to flow in and flow out, and a sealing plug attached to the opening portion so as to seal the opening portion, wherein the sealing plug is provided with a deforming element that has a deforming wall that is formed so as to be able to extend in a lower direction in the tip-shaped container in accordance with pressing from an outside and is formed so as to be urged to shrink or be able to shrink in an upper direction and that is provided so as to be positioned inside of the tip-shaped container, and a dispensing head configured to suck and discharge liquid from and into the deforming element-included dispensing tip by deforming the deforming element of the deforming element-included dispensing tip.

In this case, the "sucking and discharging" means suction and/or discharge. The reason why the deviation of the inlet unit of the deforming element-included dispensing tip can be prevented by just attaching the tip-shaped container is because, in the deforming element-included dispensing tip, the deforming element having the deforming wall deforming during the sucking and discharging is included in the tip-shaped container, and the deforming element is not related to the external wall of the tip-shaped container, and therefore, when only the tip-shaped container is attached to the dispensing head, the deviation of the inlet unit forming a part of the tip-shaped container can be prevented. Therefore, this can be attached just like an ordinary cylinder-type dispensing tip.

A sixteenth invention relates to the deforming element-included dispensing device further comprising a container group having a plurality of containers capable of accommodating various kinds of solutions and a head moving unit configured to move the dispensing head relatively with respect to the container group, and wherein the inlet units can be inserted into the containers at a time.

In this case, when the inlet unit is disposed to face the lower side, then, the suction, the discharge, and the transition of the liquid can be smoothly performed. The "solution" includes liquids including various kinds of reagents, samples, chemical substances, or magnetic bodies. The "container" includes a container having multiple liquid accommodation units and wherein each liquid accommodation unit is provided at the position corresponding to the inlet unit.

A seventeenth invention relates to the deforming element-included dispensing device, wherein the dispensing head comprises a tip support portion capable of supporting the one or more deforming element-included dispensing tips, and a movable member provided so as to be capable of being in contact with or connected with the deforming element provided with the sealing plug of the deforming element-included dispensing tip, and capable of performing forward/backward moving operation at a time along a predetermined deforming direction of the deforming element by coming into contact with or connected with the deforming element.

The movable member deforms the deforming element by performing forward/backward moving operation while it is in a state of being in contact with, contact with and detached from, or connected with the deforming element. In order to support the deforming element-included dispensing tip, support is provided to prevent the deviation and the movement of the tip-shaped container formed with only the non-deforming wall in the deforming element-included dispensing tip against the force applied by the movable member in two directions which are the extension direction and the shrinking direction in the inside thereof. In a case of the deforming element-included dispensing tip, the deforming element is included in the tip-shaped container, and the deforming element deforms in the vertical direction, and therefore, like a cylinder-type dispensing tip, it is sufficient to provide support so as to sandwich in the vertical direction. It should be noted that the tip support portion of the dispensing head may include the tip arrangement holding unit capable of arranging and detachably holding two or more deforming element-included dispensing tips with a predetermined interval in a line or a planar manner, or may include the deforming element-included dispensing tip cartridge.

An eighteenth invention relates to the deforming element-included dispensing device, wherein the deforming element-included dispensing tip comprises a hold-down plate attached to the tip-shaped container at the upper side of the sealing plug and holding each of the sealing plugs from the upper side, and the hold-down plate is provided with an operation hole in association with each of the sealing plugs, and a protection wall formed so as to extend in the lower direction from the peripheral portion of the operation hole and so as to be surrounded by the deforming element, wherein the movable member is provided to capable of be in contact with or connected with the deforming element via the operation hole.

A nineteenth invention relates to the deforming element-included dispensing device, wherein the dispensing head or the container group comprises a magnetic force unit capable of giving or removing a magnetic field into/from the inside of the tip-shaped container or the containers.

Therefore, for example, when a suspension in which many magnetic bodies holding biological chemical compounds such as protein, peptide, amino acid, DNA, RNA, oligonucleotide, and sugar chain are suspended is sucked from or discharged to the inside of the deforming element-included dispensing tip or accumulated therein, the magnetic field is given to the inside, so that the magnetic bodies are adsorbed to the inner wall of the tip, and the biological chemical compounds can be therefore separated.

A twentieth invention relates to the deforming element-included dispensing device comprising a control unit configured to control deforming of the deforming element and/or movement between the dispensing head and the container group on the basis of a number of deforming element-included dispensing tips or a structure thereof, a liquid which is to be sucked or discharged, a substance included therein, an amount thereof, an accommodation position thereof, a temperature or a concentration thereof, a processing content, or an instruction.

The substance includes not only biological materials such as nucleic acid, protein, sugar chain, amino acid, and the like but also various kinds of chemical substances including metal and the like. The "liquid" includes a solution and a suspension. The suspension includes, for example, a suspension of magnetic bodies capable of being bonded with various kinds of substances due to reaction or bonded therewith due to reaction. The "processing" includes, for example, DNA extraction processing, immunity chemical inspection, analysis processing of various kinds of biological materials, and the like.

A twenty first invention relates to the deforming element-included dispensing device comprising a control unit configured to control deforming of the deforming element on the basis of a change in terms of the positon with respect to the deforming element, and a predetermined change of the deforming element based on a change in terms of the positon.

The "change in the position of the deforming element" is a change that can be applied to the deforming element from the outside of the deforming element-included dispensing tip, and means a change in the position coordinate at the contact point or the connection point that is caused due to contact or connection of the movable member and the like. In a typical case, this means a one-dimensional change in the position along the deforming direction of the deforming element, and more specifically, this means extension or shrink of the deforming element. The extension or shrink of the deforming element depends on the amount of movement of the movable member achieved by the motor in a case where this is done by moving the movable member reciprocally using the motor.

The "predetermined change of the deforming element" is a change other than the change in the position and includes one or more changes selected from, for example, a change in the volume of the deforming element itself, a change in the size of area of a cross section perpendicular to the deforming direction of the deforming element, a thickness of the deforming element itself, a change of the surface area of the deforming element, or a change in the time of the deforming element.

More specifically, the volume of the area surrounded by the inner wall of the tip-shaped container and the inner wall of the deforming element is the area capable of accommodating the fluid, and the volume thereof cannot be correctly determined from the length in the axis direction of the deforming element due to the extension and shrink of the deforming element on the assumption that the size of area of a cross section perpendicular to the axis direction of the deforming element is constant. Therefore, a high accuracy of volume is obtained in view of not only the extension and shrink in the axis direction of the deforming element but also a change of shrink, expansion, and the like in the cross section perpendicular to the axis direction caused thereby. However, these changes are changed because of complicated factors, and therefore, it is difficult to uniquely determine the changes from calculation. Therefore, at multiple points, the relationship between the amount of the motor movement and the suction amount is measured, and the each measurement point is complemented by an approximate expression. As the approximate expression for complementation, the optimum approximate expression is chosen from a primary expression (broken line), a polynomial expression, a spline interpolation, and the like in accordance with the required control precision and the shape of the tip.

The motor control of the suction and discharge amount is performed with a high precision in accordance with a conversion expression of the suction amount and the motor control amount obtained in this manner. Further, in a case where there are hysteresis characteristics (in a case where there is a difference in the control amount between discharge and suction), multiple conversion expressions, e.g., a conversion expression for suction and a conversion expression for discharge, are prepared, and are selectively used in accordance with the situation at that moment.

For example, when the deforming wall of the deforming element has an elastic member, the deforming of the deforming element is controlled in view of the change in the volume of the fluid accommodatable area of the tip-shaped container due to a change in the thickness of the deforming wall.

Further, in a case where there are hysteresis characteristics in the deforming element as a change in time of the deforming element, the motor control amount differs between the suction and the discharge, and it is necessary to perform control using multiple conversion expressions, e.g., a conversion expression for suction and a conversion expression for discharge.

"Controlling based on something" means that control is performed by determining, for example, the change in the volume of the fluid accommodatable area of the tip-shaped container, and more specifically, the change in the volume of the area capable of accommodating fluid (gas and liquid) in tip-shaped container which is the spatial area surrounded by the inner wall surface of the tip-shaped container and the inner wall surface of the sealing plug (including the inner wall surface at the tip-shaped container inner side of the deforming element).

A twenty second invention relates to the deforming element-included dispensing device, wherein a predetermined reference position is set with regard to deforming of the deforming wall, and the deforming of the deforming wall is controlled with reference to the reference position.

In this case, the "predetermined reference position" is determined by the liquid amount treated in the processing, the volume that can accommodate a fluid in the used deforming element-included dispensing tip, the content of the processing, the processing precision of the deforming element-included dispensing tip, or the like.

For example, in a case where the liquid amount treated in the processing is a very small amount (for example, in a case of the order of several microliters to several hundred microliters), or the volume of the used deforming element-included dispensing tip is small, a case where the processing requires precision, or a case where the precision of the processing of the deforming element-included dispensing tip is not high, then, the reference position is adopted at the position along the deforming direction of the movable member or the deforming element when the predetermined deforming is already applied to the deforming element of the deforming element dispensing tip. Therefore, the control can be performed with a high degree of precision. In this case, for example, it is preferable to configure setting so as to be able to discharge all the predetermined maximum suction amount of the liquid into the deforming element-included dispensing tip according to the predetermined maximum extension amount. Therefore, this can prevent the residual of the liquid in the deforming element-included dispensing tip because of the discharge of the liquid from the deforming element-included dispensing tip.

For example, the volume of the inside of the deforming element-included dispensing tip defined in advance is denoted as V0, the distal end position in the extension direction of the movable member or the deforming element corresponding to the state is adopted as a reference, the maximum inside volume defined in advance according to the deforming of the deforming element-included dispensing tip is denoted as V1, and the minimum inside volume defined in advance according to the deforming of the deforming element-included dispensing tip is denoted as V2 (V1>V0>V2). In this case, it is preferable to set the reference position so that the predetermined maximum suction amount V1−V0 of the liquid into the deforming element-included dispensing tip satisfies such relationship that the predetermined maximum suction amount V1−V0 of the liquid into the deforming element-included dispensing tip is less than the predetermined maximum discharge amount V0−V2, and more specifically, V1−V0 is less than the predetermined maximum discharge amount V0−V2, and more specifically, V1−V0≤V0−V2 holds, and more specifically, (V1+V2)/2≤V0 holds.

In this case, since this is the "predetermined maximum deforming amount", it may not necessarily be the physically maximum deforming amount. On the contrary, when the maximum inside volume V1 and the minimum inside volume V2 are defined, it needs to be set in a range in which shrinking and urging are maintained in a case where the deforming element uses a shrinkable elastic member made of rubber and the like. More specifically, this is because, when the extension of the deforming element is configured to be large (V2 is configured to be smaller), the elastic member is stretched beyond the limit and may not be able to be restored back to the original shrink state.

Since "all the maximum suction amount can be discharged", the "maximum discharge amount" needs to have an amount equal to or more than the "maximum suction amount". Therefore, the processing can be performed without worrying about the remaining amount of the liquid in the deforming element-included dispensing tip.

On the other hand, when the amount of the treated liquid is large (for example, in the case of the order of several milliliters) or in the case where the processing does not require so much precision, control can be performed by referring to the position of the non-deforming state which is not deformed in the deforming element-included dispensing tip. In such case, for example, this is a case where the position along the deforming direction and in the state where the movable member has not come into contact with the deforming element-included dispensing tip (for example, the position away from the tip by one millimeter) is taken as the reference position.

A twenty third invention relates to the deforming element-included dispensing device, wherein the dispensing head or container group comprises a tip arrangement holding unit arranging two or more deforming element-included dispensing tips with a predetermined interval in a line or a planar manner and capable of detachably holding the two or more deforming element-included dispensing tips, or a deforming element-included dispensing tip cartridge connecting two or more deforming element-included dispensing tips by arranging the two or more deforming element-included dispensing tips with a predetermined interval in a line or planar manner.

In this case, the "planar manner" is, for example, a matrix form, a circumference shape, multiple concentric circles, and the like.

The "matrix form" has an arrangement of two directions, i.e., a row direction and a column direction, and the directions do not need to be necessarily perpendicular to each other. The "predetermined interval" has an interval corresponding to the liquid accommodation unit of the container provided in the container group. It is possible to prepare those having various kinds of pitches and numbers according to the number of treated solutions and the types and the amounts.

A twenty fourth invention relates to the deforming element-included dispensing device, wherein the deforming element-included dispensing tip cartridge is provided with dispensing head suspension engagement units at both ends along the arrangement direction thereof, and the dispensing head is provided with a frame body capable of surrounding one or more deforming element-included dispensing tip cartridges so as to surround, from the upper side, a portion of the deforming element containing portion by an upper surface portion and both side surface portions, and a support portion capable of detachably supporting the deforming element-included dispensing tip cartridge by engaging with the suspension engagement unit at a lower side of the both side surface portion of the frame body, wherein in a case where the deforming element-included dispensing tip cartridge is supported, the movable member is provided to be capable of be in contact with or connected with the deforming element of each of the deforming element-included dispensing tips via the upper surface portion.

The deforming element-included dispensing tip cartridge is preferably held in the height range of the deforming element containing portion which may change according to the deforming operation. In this case, the first engagement unit corresponds to the dispensing head suspension engagement unit.

The deforming element-included dispensing tip cartridge is preferably arranged with not only the dispensing head suspension engagement unit at each of both ends along the arrangement direction but also the rack loading engagement unit. In this case, the rack loading engagement unit corresponds to the second engagement unit. Therefore, the dispensing head suspension engagement unit is provided at the first height, and the rack loading engagement unit is provided at the second height lower than the first height. The upper surface portion and both side surface portions may be plate-like walls, or may be formed with those in which the gap occupies almost all the area such as a mesh, a frame, and the like.

A twenty fifth invention relates to the deforming element-included dispensing device, wherein the tip arrangement holding unit comprises a plate provided with two or more penetrating holes provided with a predetermined interval in a line or a planar manner, and the deforming element-included dispensing tips are inserted into the penetrating holes and held there, and the inlet unit of the deforming element-included dispensing tip penetrates through the penetrating hole to be located below the plate, so that the sealing plug is held at an upper side of the plate.

A twenty sixth invention relates to the deforming element-included dispensing device, wherein the deforming element-included dispensing tip comprises an inner portion detection area, and the dispensing head is provided with a light detection unit detecting a state of the inside through the inner portion detection area.

The "inner portion detection area" means an area for confirming or measuring the inside state. More specifically, this means an area for, e.g., confirming the sucking and discharging of the liquid (confirmation of presence/absence of the liquid), confirming the dispensing amount (confirmation of the liquid level), or measuring the carriers enclosed in the tip. Therefore, the area is preferably formed so as to easily emit light into the inside and allow the light to penetrate through the inside. For example, it is formed to have a high degree of translucency without light diffuse reflection nor any optical distortion of the tip.

In this case, the "inner portion detection area" of the deforming element-included dispensing tip is preferably provided in the narrow tube portion or the accumulation portion of the tip-shaped container. Therefore, when the inner portion detection area of the deforming element-included dispensing tip is located below the plate, the light detection unit is also configured to be located below the plate.

When the carriers are enclosed, it is preferable to provide a carrier-enclosed deforming element-included dispensing tip comprising a tip-shaped container formed with a non-deforming wall having an opening portion at an upper side and an inlet unit at a lower side for allowing fluid to flow in and flow out, and a sealing plug attached with the opening portion so as to seal the opening portion, and the sealing plug is provided with a deforming element having a deforming wall formed so as to be urged to shrink or be capable of shrinking in the upper direction and capable of extending in the lower direction in the tip-shaped container in accordance with a pressing force from the outside, and carrier bonded with or capable of being bonded with a predetermined substance enclosed in the tip-shaped container is provided. Further, it is preferable to have the hold-down plate. It is also possible to form the cartridge by coupling.

At this occasion, for example, the carrier is preferably enclosed in the narrow tube portion or the accumulation portion of the tip-shaped container. In this case, the "enclosing of the carrier in the narrow tube portion or the accumulation portion" means that the carrier accommodated in the narrow tube portion or the accumulation portion is held so as not to flow out of the narrow tube portion or the accumulation portion via the inlet unit and the like.

It should be noted that there are various kinds of carriers, and the applicant of the present application has already filed PCT/JP2002/001147, PCT/JP2004/001001, PCT/JP2005/007508 with regard to string-like carriers, and has already filed PCT/JP2005/022775 (WO 2006/062235 A1), PCT/JP2006/317337 (WO 2007/029616) with regard to particle-like carriers, and has already filed PCT/JP2005/022776 (WO 2006/062236 A1) with regard to planar carriers, and has already filed PCT/JP2006/300064 (WO 2006/073170) with regard to block-shaped carriers, and has already filed PCT/JP2007/061805 (WO 2007/145208) and the like with regard to other carriers such as line-shaped, stick-shaped, flat plate-shaped, block-shaped, or particle-like carriers.

A twenty seventh invention relates to the deforming element-included dispensing device, wherein the magnetic force unit provided with the dispensing head comprises two or more magnets provided to be able to come close to and be departed from the tip-shaped containers of one or more deforming element-included dispensing tips at a time.

For example, when the dispensing head comprises the tip support portion, and the tip support portion supports two or more deforming element-included dispensing tips by attaching the tip arrangement holding unit arranging the two or more the deforming element-included dispensing tips with a predetermined interval in a matrix form and capable of detachably holding the two or more the deforming element-included dispensing tips in such a manner that the deforming element of each deforming element-included dispensing tip can be deformed, the magnetic force unit comprises at least one comb-shaped member or (the number of columns+1) comb-shaped members or (the number of rows+1) comb-shaped members at most provided to be able to move relatively in the row direction or the column direction of the deforming element-included dispensing tips capable of being arranged in the matrix form and provided to have such a width that each can be inserted between the columns or the rows in association with the predetermined interval and extend in the row direction of the column direction, and a support member coupled with one end of the comb-shaped member, and each of the comb-shaped members is provided with as many magnets as the number of rows or the number of columns arranged with the predetermined interval at the position corresponding to each of the deforming element-included dispensing tips. When the magnetic field is given to the deforming element-included dispensing tip, all the magnets may be moved so that all the magnets come to the shortest distance to all the deforming element-included dispensing tips, and when the magnetic field is removed or weakened, all the magnets may be completely retracted from the tip arrangement holding units arranged with the deforming element-included dispensing tips, or may be moved so that each magnet is at the intermediate position of the predetermined interval of the deforming element-included dispensing tips. It is sufficient to have only about half the number of comb-shaped members as long as the magnets arranged in a single comb-shaped member affect two tips arranged at both sides thereof. It should be noted that the relative movement path of each magnet provided on the comb-shaped member with respect to the tip is along a straight line or a curved line without crossing each tip.

A twenty eighth invention relates to the deforming element-included dispensing device, wherein in a state of capable of coming into contact with a fluid that flows in and out, a carrier bonded with or capable of being bonded with a predetermined substance is enclosed in an area which is inside of the tip-shaped container and where the inside can be measured from the outside.

A twenty ninth invention relates to a deforming element-included dispensing processing method comprising a holding step of holding one or more deforming element-included dispensing tips at a dispensing head, the deforming element-included dispensing tip comprises a tip-shaped container formed with a non-deforming wall having an opening portion at an upper side and an inlet unit at a lower side for allowing fluid to flow in and flow out, and a sealing plug attached to the opening portion so as to seal the opening portion are provided, and in the sealing plug, a deforming element that has a deforming wall that is formed so as to be able to extend in a lower direction in the tip-shaped container in accordance with pressing from an outside and that is formed so as to be urged to shrink or be able to shrink in an upper direction, and the deforming element is formed so as to be located inside the tip-shaped container, a movement step of moving the dispensing head, and a deforming step of inserting the inlet unit into a container in the container group, and deforming the deforming wall surface at a time.

In this case, in the deforming step, it is preferably detected whether processing is performed in accordance with instructions or not by detecting the inside state of the deforming element-included dispensing tip or detecting absence/presence of liquid in the tip or the height of the liquid level.

A thirtieth invention relates to the deforming element-included dispensing processing method, wherein in the holding step, a tip arrangement holding unit arranging two or more deforming element-included dispensing tips with a predetermined interval in a line or a planar manner and capable of detachably holding the two or more deforming element-included dispensing tips or the deforming element-included dispensing tip cartridge arranging and coupling two or more deforming element-included dispensing tips in a line or a planar manner with a predetermined interval is attached to a dispensing head so that the deforming element-included dispensing tip can deform.

A thirty first invention relates to the deforming element-included dispensing processing method, wherein in the deforming step, a predetermined reference position is set with regard to deforming of the deforming wall surface, and the deforming of the deforming wall surface is controlled with reference to the reference position.

A thirty second invention relates to the deforming element-included dispensing processing method, wherein the deforming step comprises a step of bringing the movable member to be in contact with or connected with the deforming element of the sealing plug, and a step of lowering the movable member and/or raising the movable member.

A thirty third invention relates to the deforming element-included dispensing processing method, wherein the deforming step comprises a step of providing an operation hole in association with each of the sealing plugs in a hold-down plate for holding each of the sealing plugs from the upper side and attached to the tip-shaped container at the upper side of the sealing plug and a protection wall formed so as to extend in the lower direction from the peripheral portion of the operation hole and so as to be surrounded by the deforming element, and the movable member is brought into contact with or connected with the deforming element through the operation hole.

A thirty fourth invention relates to the deforming element-included dispensing processing method comprising a step, in which a magnetic body capable of being bonded with a predetermined substance or bonded with a predetermined substance is suspended in the liquid, and the magnetic body is separated by causing the magnetic body to be adsorbed to the inner wall of the container or the accumulation portion by giving a magnetic field into an inside of a container of the accommodation unit or the container group.

A thirty fifth invention relates to the deforming element-included dispensing processing method, wherein in the step of attaching the deforming element-included dispensing tip cartridge to a dispensing head, dispensing head suspension engagement units provided at both ends of the cartridge along an arrangement direction of the deforming element-included dispensing tips are, by moving the dispensing head, engaged with support portions of a lower side of both side surface portions of a frame body provided on the dispensing head and having an upper surface portion and the both side surface portions, and the deforming element-included dispensing tip cartridge is supported in such a manner that the frame body surrounds the upper side of the deforming element-included dispensing tip cartridge so as to include a part of the deforming element containing portion thereof in the upper side, and in the deforming step, the movable member is brought into contact with or connected with the deforming element of each of the deforming element-included dispensing tips through the upper surface portion.

A thirty sixth invention relates to the deforming element-included dispensing processing method, wherein in a state of capable of coming into contact with a fluid that flows in and out, a carrier bonded with or capable of being bonded with a predetermined substance is enclosed in an area which is inside of the tip-shaped container and where the inside can be measured from the outside, and a detection step of detecting an optical state in the tip-shaped container is further provided.

Advantageous Effects of Invention

According to the first invention, the ninth invention, the fifteenth invention, or the twenty sixth invention, the deforming element included inside of the tip-shaped container provided at the sealing plug of the tip-shaped container formed with the non-deforming wall is mechanically deformed, so that the liquid can be sucked and discharged.

Therefore, the deforming of the deforming element is guided along the inner wall of the tip-shaped container, so that the deforming element is prevented from deforming unintendedly, and highly reliable deforming can be achieved. Therefore, it is not necessary to achieve deforming by separately providing a holder for holding the tip-shaped container, like the case where the deforming wall is provided outside of the tip-shaped container.

Since the deforming element is included in the tip-shaped container formed with the non-deforming wall even during the deforming, the entire length in the axis direction can be shortened as compared with a deforming-type dispensing tip capable of accommodating the same amount of liquid. Then, the entire size of the device treating the deforming element-included dispensing tip can be reduced.

The dispensing processing can be achieved without using any complicated fluid mechanical system such as piping for passing liquid or gas including a cylinder, and this reduces the size of the device and simplifies the structure. Therefore, the device can be manufactured at a low cost and easily. In addition, a cylinder and the like having as much volume as a volume in the dispensing tip is not used, and therefore, in spite of the small size, a large quantity of liquid can be also treated.

The liquid processing such as suction, discharge, and the like is performed by deforming the deforming element included in the tip-shaped container, and therefore, there is no need to have engagement, sliding, and the like between members, which are required when a cylinder is used, and for this reason, a high degree of processing precision is not required, and the production is easy. In addition, complete watertightness and airtightness are obtained, and this reliably prevents cross contamination, and therefore, highly reliable processing can be performed.

The deforming element having the deforming wall is included inside of the tip-shaped container formed with the non-deforming wall, and the external force for deforming the deforming wall is directly applied to the deforming element, and is not directly applied to the tip-shaped container. Therefore, when an external force is applied to extend the deforming element capable of extending in the lower direction, it is sufficient to provide support so as not to move the tip-shaped container in the vertical direction, and therefore, a simple support structure is used, and the deviation of the inlet unit is prevented, and therefore, highly reliable position control can be performed.

In the deforming element-included dispensing tip according to the present invention, the deforming element having the deforming wall is included in the tip-shaped container, and therefore, the amount of air accommodated in the inside of the tip is limited to the amount of air accommodated in a portion still smaller than the portion surrounded by the inner wall of the tip-shaped container. On the other hand, in a case of a cylinder-type dispensing tip used to connect with a cylinder via a nozzle, the amount of air in not only the inside of the tip-shaped container but also the inside of the nozzle is further added to the amount of air sucked into the cylinder, and when the deforming element is provided to project out of the tip-shaped container, the amount of air in not only the inside of the tip-shaped container but also the portion surrounded by the deforming element is added. Therefore, when the liquid is sucked and discharged using the tip-shaped container of the same volume, an air gap above the liquid level of the liquid accommodated inside of the tip is small. Therefore, in the deforming element-included dispensing tip and the like according to the present invention, the precision of the control of the sucking and discharging can be enhanced as a whole even in a case where there is a change in the shape and the thickness of the deforming element in the deforming of the deforming element, the precision of the control of the sucking and discharging can be enhanced as a whole.

The deforming element having the deforming wall is included inside of the tip-shaped container formed with the non-deforming wall, and therefore, even if multiple deforming element-included dispensing tips are disposed in close contact with each other, they are not in contact with each other regardless of presence/absence of deforming of each deforming element included in each dispensing tip, and the deforming element-included dispensing tips can be integrated with a high degree of density.

When the deforming element-included dispensing tips are integrated, multiple deforming element-included dispensing tips can be deformed under the same condition at a time, and therefore, by using the deforming element-included dispensing tips, highly accurate position control and sucking and discharging control with a high degree of reproducibility can be performed. In addition, multiple processing can be performed in parallel using the deforming element-included dispensing tips, which is efficient, and even if many containers are arranged in close contact with each other, highly reliable processing can be performed.

Since the deforming element having the deformable deforming wall is included inside of the tip-shaped container formed with the non-deforming wall, this prevents unnecessary external force from being applied to the deforming element except the deforming applied to the deforming element in order to suck and discharge the fluid. Therefore, the deforming element is protected to prevent damages, destruction, or deforming of the deforming element caused by unintended external force, or other unintended heating from the outside, change in the quality caused by chemical substances from the outside, and the management and the handling of the deforming element-included dispensing tips can be facilitated.

According to the second invention or the tenth invention, the deforming element containing portion capable of accommodating the deforming element is separately provided from the accumulation portion or the narrow tube portion accumulating the liquid, so that this makes it easy to prevent the contact between the deforming element and the liquid and entry of the liquid into the deforming element containing portion, and the liquid is prevented from remaining in the tip, and a high degree of quantitative reliability in the sucking and discharging of the liquid can be ensured. In addition, the cross contamination due to the liquid remaining in the tip can be prevented.

According to the third invention or the eleventh invention, in the sealing plug, the tubular wall formed with the side wall and the bottom wall having the deforming wall is provided so as to protrude inside of the tip-shaped container, and the depression is formed outside, so that the deforming guided by the inner wall of the tip-shaped container is performed, and therefore, the range of the deforming is limited or restricted in the tip-shaped container, and a highly reliable deforming can be performed.

The external force is caused to be exerted on the bottom wall of the depression provided in the sealing plug, and therefore, the force can be applied in a stable state, and a highly reliable deforming can be performed.

According to the fourth invention, the twelfth invention, the eighteenth invention, or the thirty third invention, the sealing plug is held from the upper side, and the deforming element is prevented from projecting to the outside of the tip-shaped container, and in addition, when the deforming element is deformed, abrasion of the deforming wall due to contact of the movable member to the deforming wall and the degradation caused by wear are prevented, and during the forward/backward moving operation of the movable member unit, the resistance received from the deforming wall due to contact with the deforming wall is removed or alleviated, and smooth deforming operation can be performed. In addition, by preventing unexpected deforming from being given to the deforming element, highly reliable deforming control can be performed.

According to the fifth invention, in the deforming element, the depression surrounded by the tubular wall projecting to the inside having the deforming wall forming the bellows on the side wall made of the flexible member, is formed, and is deforming with the bellows. Therefore, the size of the surface area and the thickness of the deforming wall surface caused by the deforming are not changed, and the deforming of the bellows is guided by the tip-shaped container, and the deforming having a high degree of quantitative reliability can be performed. In addition, since the deforming element is formed of a rigid member, and therefore the deforming element is less likely to be broken. Further, the bending portion and the direction by the deformation are determined, and the regularity of the deforming and the quantitative reliability caused by the deforming are high.

According to the sixth invention, the deforming element is formed so as to have the deforming wall formed with the elastic member and have the depression surrounded by the tubular wall projecting to the inside of the tip-shaped container. Therefore, even if the deforming element is extended, the deforming element can be easily shrink by removing the external force, and returned back to the original state, and therefore the responsiveness is high.

According to the seventh invention, the sealing plug has the elastic member, and is attached to the opening portion of the tip-shaped container with the O ring interposed therebetween, and therefore, without being attached in a non-detachable manner by adhesion and welding, the sealing plug can be detachably attached to the opening portion of the tip-shaped container while maintaining airtightness and watertightness.

According to the ninth invention, in a case where multiple tip-shaped containers are integrally coupled so as to be partitioned from each other and from the outside by using the non-deforming wall, the deforming element having the deforming wall is included in the tip-shaped container, and therefore, each can be deformed without being affected by the coupling. Therefore, multiple deforming element-included dispensing tips can be integrated with a high density.

According to the sixteenth invention, a required reagent and the like are accommodated in the container in advance, and therefore, the dispensing processing can be automated easily.

According to the seventeenth invention or the twenty ninth invention, the movable member is brought into contact with or connected with the deforming element, and can be moved along the deforming direction of the deforming element, so that by using only the mechanical mechanism without contact with a processing target liquid, the processing such as suction, discharge, transition, and the like can be performed, and the portion that can come into contact with the liquid is limited to the inside of the tip-shaped container surrounded by the non-deforming wall, and therefore, the cross contamination can be reliably prevented.

Further, the movable member can be brought into contact with or connected with the deforming element included inside of the tip-shaped container, and the deforming element can be guided to the tip-shaped container formed with the non-deforming wall, and therefore, the deforming element can be deformed in a stable state, and highly reliable processing can be performed.

According to the nineteenth invention or the thirty fourth invention, the magnetic field is given to or removed from the inside of the accommodation unit or the container, and therefore, the magnetic bodies in the liquid in which the magnetic bodies are suspended are separated by being adsorbed to the inside, and therefore, processing including separation processing can be automated throughout.

According to the twentieth invention, the deforming of the deforming element and/or the movement of the dispensing head are controlled on the basis of the structure and the like of the deforming element-included dispensing tip, and therefore, the sucking and discharging can be done with a high degree of precision in quantitative reliability.

According to the twenty first invention, when the control unit controls the deforming of the deforming element according to the change in the position with respect to the deforming element, the movable member is brought into contact or connected at the end of the deforming element to perform deforming in view of the change in the deforming element itself, and therefore, the sucking and discharging can be performed with a high degree of precision of quantitative reliability regardless of the simple structure.

According to the twenty second invention or the twenty eighth invention, the deforming is performed on the basis of the reference position capable of at least one of extension and shrinking of the deforming element, and therefore, for example, when both of extension and shrinking of the deforming element are possible, the processing can be performed efficiently and swiftly while immediately coping with both of them. By setting the reference position is a suitable manner, it is possible to prevent the liquid from remaining in the deforming element-included dispensing tip as a result of discharge of the liquid.

According to the twenty third invention or the thirtieth invention, multiple deforming element-included dispensing tips are arranged in the tip arrangement holding unit, or coupled deforming element-included dispensing tip cartridges are adopted as a unit and provided in the dispensing head or the container group and configured to be movable, so that the deforming element-included dispensing tips can be replaced swiftly, and the efficiency of the processing can be enhanced.

According to the twenty fourth invention or the thirty second invention, the dispensing head is moved by the head movement mechanism, so that the deforming element-included dispensing tip cartridge can be detachably attached to the frame body, and therefore, it is not necessary to provide dedicated attachment mechanism, and the increase in the size of the device can be prevented. Depending on necessary, any number of deforming element-included dispensing tip cartridges can be attached, and therefore, efficiently control can be performed.

According to the twenty fifth invention, multiple penetrating holes are provided through the plate as the tip arrangement holding unit, and the deforming element-included dispensing tips are inserted into the penetrating holes to be held therein, and therefore, the deforming element-included dispensing tips can be arranged easily.

According to the twenty sixth invention, the state of the inside of the deforming element-included dispensing tip is detected, whereby whether the suction and discharge are performed accurately according to an instruction is confirmed by checking the presence/absence of the liquid and the water level of the liquid, and therefore, highly reliable processing can be performed.

According to the twenty seventh invention, magnets can be provided to be able to come close to and be departed from the tip-shaped containers of the deforming element-included dispensing tips at a time, and therefore, with a simple structure, the magnetic field can be easily applied to each deforming element-included dispensing tip at a time.

According to the eighth invention, the fourteenth invention, the twenty eighth invention, or the thirty sixth invention, the effects explained above are achieved, and in addition, the carriers that are bonded with or that can be bonded with various kinds of substances such as biological materials are enclosed in the tip-shaped carrier, and the deforming elements are mechanically deformed, so that the liquid can be sucked and discharged. Therefore, without using any complicated fluid mechanical mechanism such as piping and the like for passing liquid or gas such as a cylinder, suction of fluid into the tip-shaped container, contact between the fluid and the carrier, and the discharge are enabled, and by using a device that is easily operated, manually, or with a simple structure, the device can be produced and the processing can be performed at a low cost and easily.

While the carriers that are bonded with or that can be bonded with the predetermined substance are enclosed in the tip-shaped container having the inlet unit, various kinds of processing, for example, reaction, cleaning, temperature control, separation, agitation, dispensing, clearness, isolation, elution, and extraction can be performed by just sucking and discharging the liquid and moving the carrier-enclosed deforming container, and therefore, the processing can be performed efficiently, swiftly, and easily.

Further, according to the present invention, the reaction with the predetermined substance bonded with the carriers to the measurement thereof can be performed while still enclosed inside of the deforming element-included dispensing tip of which opening is only the inlet unit, and therefore, throughout the object processing, the predetermined substance is not contacted by another member or a person, and the processing can be performed, and therefore, while preventing cross contamination, the processing can be performed reliably with a high degree of reliability. In order to have a shape suitable for the liquid amount to be treated and the speed of the fluid, the carrier-enclosed deforming container is selected, so that various kinds of processing can be coped with, and therefore, there is versatility and variations.

According to the present invention, the carriers are enclosed in the tip-shaped container and held therein, and therefore, this is not the case where they are moved by applying fluid force, and treating of the carriers and the measurement of the optical state can be facilitated using a simple control without performing complicated synchronization control and the like.

As explained above, the "area where the inside can be measured from the outside" corresponds to the "inner portion detection area".

BRIEF DESCRIPTION OF DRAWINGS

FIGS. 1(a) and 1(b) are top views and cross sectional views taken along line A-A showing deforming element-included dispensing tips of a smaller volume according to a first embodiment of the present invention.

FIGS. 2(a) to 2(d) are top views and cross sectional views taken along line A-A showing deforming element-included dispensing tips of various volumes according to the first embodiment of the present invention.

FIGS. 3(a) to 3(d) are explanatory diagrams illustrating operation of a deforming element-included dispensing tip according to the first embodiment of the present invention.

FIG. 4 is a perspective view illustrating a deforming element-included dispensing device according to the second embodiment of the present invention.

FIGS. 5(a) and 5(b) are a top view and a cross sectional view taken along line A-A showing the deforming element-included dispensing device of FIG. 4.

FIGS. 6(a) and 6(b) are partially enlarged view illustrating the deforming element-included dispensing devices of FIG. 3 or FIG. 4 and a perspective view of a corresponding portion of a conventional technique.

FIGS. 7(a) and 7(b) are a top view and a cross sectional view taken along line A-A of FIG. 5.

FIG. 8 is a perspective view illustrating eight deforming element-included dispensing tip cartridge connecting eight deforming element-included dispensing tips according to a third embodiment of the present invention.

FIG. 9 is an exploded perspective view illustrating the deforming element-included dispensing tip cartridge of FIG. 8 when seen from the above.

FIG. 10 is an exploded perspective view illustrating the deforming element-included dispensing tip cartridge of FIG. 8 when seen from below FIG. 11 is a cross sectional view illustrating the deforming element-included dispensing tip cartridge of FIG. 8.

FIGS. 12(a) and 12(b) are cross sectional views illustrating the uppermost point and the lowermost point of movable members in the deforming element-included dispensing tip cartridge of FIG. 8.

FIG. 13 is a perspective view illustrating the deforming element-included dispensing device according to a fourth embodiment of the present invention when the deforming element-included dispensing tip cartridge of FIG. 8 is attached.

FIG. 14 is an enlarged perspective view illustrating a main portion of a dispensing head of the deforming element-included dispensing device according to FIG. 13.

FIG. 15 is a back-side perspective view illustrating the deforming element-included dispensing device according to FIG. 13.

FIG. 16 is a perspective view after the deforming element-included dispensing tip cartridge according to FIG. 8 is attached to the deforming element-included dispensing device according to FIG. 13 and sucking and discharging operation is performed by applying a magnetic field.

FIG. 17 is a perspective view illustrating a dispensing head is moved while a dripping prevention tray is pulled out after operation of FIG. 13.

FIGS. 18(a) to 18(d) are cross sectional views illustrating a deforming element-included dispensing tip into which a carrier is enclosed according to a fifth embodiment of the present invention.

FIGS. 19(a) to 19(f) are cross sectional views illustrating a deforming element-included dispensing tip into which a carrier is enclosed according to another example of the fifth embodiment of the present invention.

FIGS. 20(a) and 20(b) are perspective views illustrating a light detection unit and a magnetic force unit according to the fifth embodiment of the present invention.

FIGS. 21(a) and 21(b) are perspective views illustrating a light detection unit according to the fifth embodiment of the present invention.

DESCRIPTION OF EMBODIMENTS

Subsequently, a deforming element-included dispensing tip according to the first embodiment of the present invention and a deforming element-included dispensing device according to the second embodiment using the deforming element-included dispensing tip will be explained with reference to drawings.

FIGS. 1(a) and 1(b) are top views and cross sectional views taken along line A-A illustrating deforming element-included dispensing tips 11, 11' of two types of small capacities (for example, about 100 to 200 microliters) according to the first embodiment of the present invention.

FIG. 1(a) illustrates an adhesion sealing-type deforming element-included dispensing tip 11.

The deforming element-included dispensing tip 11 comprises a tip-shaped container 15 formed with a non-deforming wall having an opening portion 14b at an upper side and an inlet unit 13 at a lower side for allowing fluid to flow in and flow out, and the deforming element-included dispensing tip 11 comprises a sealing plug 19 adhered, using an adhesive agent and the like, and attached to the opening portion 14b so as to engage with and seal the opening portion 14b, and the sealing plug 19 is provided with a deforming element 12 that can extend in a lower direction in the tip-shaped container 15 in accordance with pressing from the outside in a lower direction along an axis line of the tip-shaped container and that has a deforming wall formed so as to be urged to shrink in the upper direction.

The tip-shaped container 15 comprises a deforming element containing portion 14 having the opening portion 14b and capable of accommodating the deforming element 12 so as to encompass a deformable range of the deforming element 12, a narrow tube portion 18 having a diameter narrower than the deforming element containing portion 14 and having the inlet unit 13 that can be inserted into various kinds of external containers, an accumulation portion 16 capable of accumulating liquid sucked from the inlet unit 13 in communication with the deforming element containing portion 14 and the narrow tube portion 18 and having a diameter that is thicker than the narrow tube portion 18 but is thinner than the deforming element containing portion 14, and a cone-shaped transition unit 17 disposed between the narrow tube portion 18 and the accumulation portion 16. A flange 14c is provided outside of the opening portion 14b of the deforming element containing portion 14, and is used to support the deforming element-included dispensing tip 11 and the deforming element. In this case, for example, when the volume is 100 microliters, for example, the internal diameter of the deforming element containing portion 14 is 6 mm, the internal diameter of the accumulation portion 16 is 3 mm, and the internal diameter of the narrow tube portion 18 is 0.5 mm.

As the deforming element 12, the sealing plug 19 comprises a deforming wall formed with an elastic member such as rubber, and comprises a tubular wall comprising a bottom wall 12a and a depression 12c surrounded by the side wall 12b and projecting to the inside of the tip-shaped container 15. Reference numeral 14a is a bottom inlet unit of the deforming element containing portion 14, and is formed in a tapered manner to become narrower toward the accumulation portion 16. The sealing plug 19 may be attached with not only adhesion but also thermal adhesion and ultrasonic adhesion. Since the sealing plug 19 is attached to the opening portion 14b by adhesion, welding, and the like, the sealing plug 19 cannot be detached from the tip-shaped container 15.

FIG. 1(b) illustrates an O ring sealing-type deforming element-included dispensing tip 11'.

Hereinafter, the same elements as the deforming element-included dispensing tip 11 are denoted with the same reference numerals, and those different therefrom are denoted with ('), so that they are distinguished from each other.

The deforming element-included dispensing tip 11' comprises a tip-shaped container 15' formed with a non-deforming wall having an opening portion 14b at an upper side and an inlet unit 13 at a lower side for allowing fluid to flow in and flow out, and a sealing plug 19' detachably attached to the opening portion 14b to seal the opening portion 14b by making use of the engagement between the O ring 19'a and the ring-shaped groove 14'd, and the sealing plug 19' is provided with the deforming element 12.

The tip-shaped container 15' comprises a deforming element containing portion 14' comprising a ring-shaped groove 14'd engaging with the O ring 19'a in proximity to the opening portion 14b and the opening portion 14b and capable of accommodating the deforming element 12, a narrow tube portion 18 having a diameter narrower than the deforming element containing portion 14' and having the inlet unit 13 that can be inserted into various kinds of external containers, an accumulation portion 16 capable of accumulating liquid sucked from the inlet unit 13 in communication with the deforming element containing portion 14' and the narrow tube portion 18 and having a diameter thicker than the narrow tube portion 18 but thinner than the deforming element containing portion 14', and a funnel-shaped transition unit 17' provided between the narrow tube portion 18 and the accumulation portion 16.

Subsequently, FIGS. 2(a) and 2(b) illustrate deforming element-included dispensing tips according to an embodiment of the present invention having various sizes of and various types of deforming wall or sealing plug attachment methods.

FIG. 2(a) illustrates an adhesion sealing-type deforming element-included dispensing tip 11 of a small volume explained in FIG. 1(a) for comparison in terms of the size.

FIG. 2(b) illustrates an adhesion sealing-type deforming element-included dispensing tip 110 of a medium volume (for example, about 300 microliters).

The deforming element-included dispensing tip 110 comprises a tip-shaped container 150 formed with a non-deforming wall having an opening portion 140b at an upper side and an inlet unit 130 at a lower side for allowing fluid to flow in and flow out, and the deforming element-included dispensing tip 110 comprises a sealing plug 190 adhered, using an adhesive agent and the like, and attached to the opening portion 140b so as to engage with and seal the opening portion 140b, and the sealing plug 190 is provided with a deforming element 120 that can extend in a lower direction in the tip-shaped container 150 in accordance with pressing from the outside in a lower direction along an axis line of the tip-shaped container 150 and that has a deforming wall urged to shrink in the upper direction.

The tip-shaped container 150 comprises a deforming element containing portion 140 having the opening portion 140b and capable of accommodating the deforming element 120 so as to encompass a deformable range of the deforming element 120, a narrow tube portion 180 having a diameter narrower than the deforming element containing portion 140 and having the inlet unit 130 that can be inserted into various kinds of external containers, an accumulation portion 160 capable of accumulating liquid sucked from the inlet unit 130 in communication with the deforming element containing portion 140 and the narrow tube portion 180 and having a diameter that is thicker than the narrow tube portion 180 but is thinner than the deforming element containing portion 140, and a funnel-shaped transition unit 170 disposed between the narrow tube portion 180 and the accumulation portion 160. A flange 140c is provided outside of the opening portion 140b of the deforming element containing portion 140, and is used to support the deforming element-included dispensing tip 110.

As the deforming element 120, the sealing plug 190 comprises a deforming wall formed with an elastic member such as rubber, and comprises a tubular wall projecting to the inside of the tip-shaped container 150 and comprising a bottom wall 120a and a depression 120c surrounded by the side wall 120b. Reference numeral 140a is a bottom inlet unit of the deforming element containing portion 140, and is formed in a tapered manner to become narrower toward the accumulation portion 160. The sealing plug 190 may be attached with not only adhesion but also thermal adhesion and ultrasonic adhesion. The sealing plug 190 cannot be detached from the tip-shaped container 150.

FIG. 2(c) illustrates an O ring sealing-type deforming element-included dispensing tip 111 of a medium volume (for example, about 300 microliters). The same elements as those of the deforming element-included dispensing tip 110 of FIG. 2(b) are denoted with the same reference numerals, and explanation thereabout is omitted.

The deforming element-included dispensing tip 111 comprises a tip-shaped container 151 formed with a non-deforming wall having an opening portion 140b at an upper side and an inlet unit 130 at a lower side for allowing fluid to flow in and flow out, and a sealing plug 191 detachably attached to the opening portion 140b to seal the opening portion 140b by making use of the engagement between the O ring 191a and the ring-shaped groove 141c, and the sealing plug 191 is provided with the deforming element 121.

The tip-shaped container 151 comprises a deforming element containing portion 141 comprising a ring-shaped groove 141d engaging with the O ring 191a in proximity to the opening portion 140b and the opening portion 140b and capable of accommodating the deforming element 121, a narrow tube portion 180 having a diameter narrower than the deforming element containing portion 141 and having the inlet unit 130 that can be inserted into various kinds of external containers, an accumulation portion 160 capable of accumulating liquid sucked from the inlet unit 130 in communication with the deforming element containing portion 141 and the narrow tube portion 180 and having a diameter thicker than the narrow tube portion 180 but thinner than the deforming element containing portion 141, and the transition unit 170. A flange 140c is provided outside of the opening portion 140b of the deforming element containing portion 141, and is used to support the deforming element-included dispensing tip 111.

As the deforming element 121, the sealing plug 191 comprises a deforming wall formed with a flexible member, and comprises a tubular wall in a substantially circular tubular shape projecting to the inside of the tip-shaped container 151 and comprising a bottom wall 121a and a depression 121c surrounded by the side wall 121b a part of which is formed with bellows. The bellows is a deforming wall disposed on a portion of the side wall 121b of the deforming element 121 so as to divide the side wall 121b to an upper side and a lower side and configured to deform in such a manner that the vertical direction is the deforming direction. The bellows is in a screw shape, and as a wave form of a screw, crests (eight crests in this example) and roots (eight roots in this example) are formed.

FIG. 2(d) illustrates an adhesion sealing-type deforming element-included dispensing tip 112 of a large volume (for example, about 3 to 5 milliliters). The deforming element-included dispensing tip 112 comprises a tip-shaped container 152 formed with a non-deforming wall having an opening portion 142b at an upper side and an inlet unit 132 at a lower side for allowing fluid to flow in and flow out, and the deforming element-included dispensing tip 112 comprises a sealing plug 192 adhered, using an adhesive agent and the like, and attached to the opening portion 142b so as to engage with and seal the opening portion 142b, and the sealing plug 192 is provided with a deforming element 122 that can extend in a lower direction in the tip-shaped container 152 in accordance with pressing from the outside in a lower direction along an axis line of the tip-shaped container 152 and that has a deforming wall urged to shrink in the upper direction.

The tip-shaped container 152 comprises a deforming element containing portion 142 having the opening portion 142b and capable of accommodating the deforming element 122 so as to encompass a deformable range of the deforming element 122, a narrow tube portion 182 having a diameter narrower than the deforming element containing portion 142 and having the inlet unit 132 that can be inserted into various kinds of external containers, and a funnel-shaped transition unit 172 disposed between the deforming element containing portion 142 and the narrow tube portion 182 and the accumulation portion 162 and having a diameter thicker than the narrow tube portion 182 but narrower than the deforming element containing portion 142. A flange 142c is provided outside of the opening portion 142b of the deforming element containing portion 142, and is used to support the deforming element-included dispensing tip 112.

The sealing plug 192 comprises a deforming wall formed with a flexible member serving as the deforming element 122, and comprises a tubular wall projecting to the inside of the tip-shaped container 152 and comprising a bottom wall 122a and a depression 122c surrounded by the side wall 122b a part of which is formed with bellows. Reference numeral 142a is a bottom inlet unit of the deforming element containing portion 142, and is formed in a tapered manner to become narrower toward the accumulation portion 162. The bellows is a deforming wall disposed on a portion of the side wall 122b of the deforming element 122 so as to divide the side wall 122b to an upper side and a lower side and configured to deform in such a manner that the vertical direction is the deforming direction. The bellows is in a screw shape.

FIGS. 3(a) to 3(d) schematically illustrate the deforming element-included dispensing tip 110 of the medium volume when it is supported by a dispensing head 70 of a deforming element-included dispensing device 10 explained later. This shows that a pin 20 of a movable member disposed on the dispensing head 70 is brought into contact with the bottom wall 120a of the deforming element 120 in the substantially circular tubular shape of the deforming element-included dispensing tip 110.

FIG. 3(a) illustrates a state in which the pin 20 is in contact with the bottom wall 120a of the deforming element 120 but deformation is not applied to the deforming element 120 (a state in which the lower end of the pin 20 is at level L1). More specifically, this indicates that the pin 20 of the movable member is moved in the upper direction from the deforming element 120 of the deforming element-included dispensing tip 110, the deforming element 120 is urged to shrink until this state is achieved. This indicates a state in which the fluid accommodatable area is a maximum volume (VL).

FIG. 3(d) illustrates a state in which the deforming element 120 is most extended and the fluid accommodatable area is a minimum volume (VS), and the lower end of the deforming element 120 is at a stop at the bottom inlet unit 140a of the deforming element containing portion 140. Therefore, this indicates a state in which no further extension is possible (a state in which the position of the lower end of the pin 20 is at level L4).

FIG. 3(b) is a maximum extension state in terms of control of the deforming element 120, and the fluid accommodatable area is a minimum volume V1 in terms of control (the position of the lower end of the pin 20 is at level L3).

FIG. 3(c) is a minimum extension state in terms of control of the deforming element 120, and the fluid accommodatable area is a maximum volume V2 in terms of control (the position of the lower end of the pin 20 at level L2). Then, in general, $VL > V2 > V1 > VS$ holds. At this occasion, by defining a reference volume V0 of the fluid receivable area in terms of control as follows, all the amount of liquid sucked into the deforming element-included dispensing tip 110 can be configured to be dischargeable.

More specifically, the maximum suction amount $V2-V0$ of the liquid sucked into the dispensing tip determined in advance is preferably configured such that the reference position satisfies a relationship less than the maximum discharge amount $V0-V1$ determined in advance, and more specifically, the reference position satisfies $V2-V0 \leq V0-V1$, i.e., $(V1+V2)/2 \leq V0$. The position of the lower end of the pin 20 corresponds to level L0 (L3<L0<L2). It should be noted that V1, V2 are in a range in which shrinkage urging of the deforming element formed with an elastic member is maintained.

FIG. 4 illustrates a perspective view of the deforming element-included dispensing device 10 according to the second embodiment using the deforming element-included dispensing tip 11 according to the first embodiment of the present invention.

The deforming element-included dispensing device 10 comprises a dispensing head 70 in which 96 deforming element-included dispensing tips 11 of the small volume arranged in a matrix form of 12 rows×8 columns is supported (96 elements are arranged in two directions, i.e., 12 rows in the column direction and 8 columns in the row direction) and which performs sucking and discharging of liquid from and to the deforming element-included dispensing tip 11 by deforming the deforming wall of the deforming element 12 of each of the deforming element-included dispensing tips 11, and 96 microplates 30 serving as a container group in which multiple wells 32 (96 wells in this case) that can accommodate various liquids, reagents, samples, and the like are arranged in a matrix form. It should be noted that the inlet units 13 of the deforming element-included dispensing tips 11 are arranged in such a manner that they can be inserted into the wells 32 at a time.

The dispensing head 70 comprises a tip support portion 24 supporting the 96 small volume deforming element-included dispensing tips 11, and the tip support portion 24 comprises a tray 22 supporting the 96 deforming element-included dispensing tips 11 and having 96 support holes 23 penetrating therethrough having an internal diameter larger than the external diameter of the deforming element containing portions 14 of the deforming element-included dispensing tips 11 arranged in the matrix form of 12 rows×8 columns but smaller than the external diameter of the flange 14c, two tray grasping arms 27 grasping the tray 22 so as to sandwich the both sides of the tray 22 so that it can be engaged therewith and detached therefrom, and a tip hold-down plate 28 having pin holes 28a arranged in a matrix form of 12 rows×8 columns and having a size smaller than the external diameter of the opening portion 14b of the deforming element-included dispensing tip 11 but in such a manner that the pin 20 is loosely inserted to reciprocally move in the vertical direction, so that the 96 deforming element-included dispensing tips 11 supported by the tray 22 is held from above. The tray 22 corresponds to the tip arrangement holding unit.

The tray grasping arm 27 is attached to the support substrate 40 of the dispensing head 70 with a link 29 of the tray grasping arm driving mechanism interposed therebetween in such a manner that the tray grasping arm 27 is slidably supported by the projection portions 27*a* and in such a manner that the tray grasping arm 27 can be departed therefrom. The tip hold-down plate 28 is attached by four tension members 26 having springs urged to press in the lower direction with respect to the support substrate 40.

The support substrate 40 of the dispensing head 70 is provided with a magnetic force unit 50. The magnetic force unit 50 includes multiple magnets (96 magnets in this example) disposed to be able to, at a time, come close to and be departed from the accumulation portions 16 of multiple deforming element-included dispensing tips 11 (96 deforming element-included dispensing tips 11 in this example).

The magnetic force unit 50 comprises six comb-shaped members 51 provided to be able to move in the row direction of the deforming element-included dispensing tips 11 arranged with a predetermined interval in the matrix form (in a case of a matrix of 12 rows×8 columns in FIG. 4) and provided to extend along the row direction and have such a width that it can be inserted every other space between each row in association with the predetermined interval, and a support member 52 coupled with one end of the comb-shaped member 51, and each of the comb-shaped members 51 is such that as many magnets (511) as the number of columns (eight magnets (511) in this example) arranged with the predetermined interval at positions corresponding to the accumulation portions 16 of the deforming element-included dispensing tips 11 are provided on both side surfaces of the comb-shaped member 51. When the magnetic field is applied to, all the magnets are moved to a position of the shortest distance to all of the deforming element-included dispensing tips 11, and when the magnetic field is eliminated, all the magnets are completely retracted from the tip support portion 24.

For the support substrate 40, a linear step motor 54 for reciprocally driving the comb-shaped member 51 is provided, and the comb-shaped member 51 is moved in the row direction by reciprocally moving the driving plate 56 coupled via a driving shaft 55, the comb-shaped member 51 and guide rods 53.

On the upper side of the support substrate 40, a movable member driving linear step motor 60 is provided to move the 96 pins 20 which are movable members in the vertical direction, so that the 96 pins 20 coupled via a driving shaft 61, a driving plate 63, and guide rods 62 of the motor 60 are moved in the vertical direction.

The support substrate 40 is provided with the vertical direction movement mechanism of the dispensing head, i.e., guide members 42 engaging with guide rails 41 disposed on a side plate 46 of a device fixed to a stage on which the microplate 30 is mounted, so that the dispensing head 70 provided on the side plate 46 can be moved in the vertical direction by the linear step motor 44 driving in the vertical direction.

FIG. 5(*a*) is a top view illustrating the deforming element-included dispensing device 10. FIG. 5(*b*) is a cross sectional view taken along line A-A of FIG. 5(*a*).

Reference numeral 29*a* denotes a step motor for driving a tray grasping arm, and by rotating a predetermined angle, the tray 22 can be grasped and released.

The 96 pins 20 are arranged in a matrix form of 12 rows×8 columns extending in the lower direction from the lower side of the plate-shaped movable member 21 coupled with the driving shaft 61 of the motor 60.

Subsequently, in a case where the deforming element-included dispensing device 10 performs various kinds of processing, for example, extraction processing of DNA, RNA, on 96 samples at a time will be explained. Multiple microplates 30 accommodating, in advance, 96 samples, a magnetic particle suspension covered with silica, and the like, nucleic acid extraction reagent solution, cleaning solution, eluate, and the like are arranged and prepared on the stage in the order of processing. Processing is performed on each of the multiple microplates 30 using, for example, a commonly used XY axis moving mechanism, not shown, such as a ball screw and a step motor while the deforming element-included dispensing device 10 hung from the upper side of the microplates 30 is relatively moved in order.

Now, a case where cleaning is going to be performed upon an already completed step of causing magnetic particles to bond DNA of an object from a sample will be explained. The dispensing device 10 is positioned, for example, above the microplate 30 accommodating cleaning solution in each well 32 and the deforming element-included dispensing tips 11 are positioned immediately above each well 32. At this occasion, magnetic particles bonded with DNA of an object in the processing of the previous step are adsorbed to the inner wall of the accumulation portion 16 of each deforming element-included dispensing tip 11 and are in a condensed state in a pellet form.

More specifically, at this occasion, six comb-shaped members 51 provided with 96 magnets provided on the dispensing head 70 of the dispensing device 10 extends along the row direction between six rows of the 96 deforming element-included dispensing tips 11 arranged in a matrix form, and are in proximity to the accumulation portions 16 of the deforming element-included dispensing tips 11.

Therefore, by driving the movable member driving linear step motor 60, the pins 20 provided so as to project in the lower direction of the movable member 21 are caused to be located in the lower direction to a reference position defined in advance, so that the deforming elements 12 of the deforming element-included dispensing tips 11 are extended in the lower direction to a state defined in advance.

Subsequently, the dispensing head 70 is descended by driving the linear step motor 44, and the inlet unit 13 of each deforming element-included dispensing tip 11 is inserted into each well 32 of the microplate 30.

Subsequently, the comb-shaped member 51 of the magnetic force unit 50 is retracted from between the rows of the deforming element-included dispensing tips 11 by the linear step motor 54, so that the magnetic fields in the accumulation portions 16 are eliminated.

Subsequently, the pins 20 are moved in the upper direction by driving the movable member driving linear step motor 60, and the pins 20 are moved to the upper limit position in terms of control defined in advance corresponding to level L2 shown in FIG. 3(*c*), so that the cleaning solution in the well 32 is sucked at a time to be introduced to the accumulation portion 16 of each deforming element-included dispensing tip 11, and it is brought into contact with the magnetic particles still condensed on the inner wall of the accumulation portion 16 in such a state that the magnetic field is removed.

Subsequently, the pins 20 are moved in the lower direction with respect to the cleaning solution and the magnetic particles introduced to the accumulation portion 16 by moving the movable member driving linear step motor 60, so that the pins 20 are moved to the lower limit position defined in advance beyond the reference position corresponding to level L3 as shown in FIG. 3(*b*), and therefore, the entire amount of cleaning solution in the accumulation portion 16 and the magnetic particles are discharged through the inlet unit 13 into the 96 the wells 32 at a time.

In this manner, the sucking and discharging are repeated until the condensation of the magnetic particles on the inner wall of the accumulation portion 16 is solved, and the magnetic particles are resuspended in the cleaning solution, and the cleaning solution and the object substance of the magnetic particles are sufficiently brought into contact and processed.

When the reaction and resuspension of the cleaning solution and the object substance are finished as described above, the comb-shaped member 51 of the magnetic force unit 50 is moved into between the rows again, and the magnetic field is given to the inside of the accumulation portion 16 of each deforming element-included dispensing tip 11. In this state, the pins 20 are moved in the upper direction to the upper limit position in terms of control by driving the movable member driving linear step motor 60, and the resuspended magnetic particle suspension is sucked and introduced to the accumulation portion 16, so that the magnetic particles are adsorbed to the inner wall by the magnetic field again.

Subsequently, the pins 20 are moved to the lower limit position in terms of control, so that all the residual liquid other than the magnetic particles adsorbed to the inner wall is discharged to each well 32 at a time, and then, the processing in this step is finished.

Then, the dispensing device 10 is moved to a microplate in a subsequent step, and subsequent processing is performed.

FIG. 6(a) and FIG. 7(a) illustrate only a portion of the tip support portion 24, the movable members 21, and the pins 20 in a case where the sucking and discharging processing is performed using the 96 deforming element-included dispensing tips 11 according to the present invention.

On the other hand, FIG. 6(b) and FIG. 7(b) illustrate a cylinder 231 and a plunger 220 in a case where sucking and discharging processing is performed using 96 dispensing tips (tip-shaped containers) 15 used by attaching the opening portions thereof to 96 nozzles 230 according to a conventional example. For comparison, in this case, the drawings are shown using the same tray 22 of tip arrangement holding unit as that of the present invention and the tip-shaped container 15 used for the deforming element-included dispensing tip 11 according to the present invention.

Then, it is understood from the sizes in the drawings that how the present invention reduces the device size and simplifies the device structure.

Further, in the device according to the embodiment of the present invention, it is not necessary to attach the dispensing tips to the nozzles by engaging the dispensing tips with the nozzles, and therefore, it is not necessary to have a force as much as about 100 kg for causing many dispensing tips, for example, 96 dispensing tips, to be engaged with the nozzles at a time, and therefore, the device according to the embodiment of the present invention is suitable for integration.

Therefore, the dispensing tip does not need a high degree of rigidity to avoid the damage of the dispensing tip due to the force applied when it is attached, or the lifetime of the tip is extended, and the burden of quality control can be simplified.

Further, the deforming element is included, and the external wall of the dispensing tip is formed with the non-deforming wall, and therefore, the higher degree of density in the integration can be achieved, and further, the integration can be achieved in an integrated manner.

Instead of moving the plunger to slide on the inner wall of the cylinder, the sealing deforming element is extended and shrunk by the movable member, and therefore, watertightness and airtightness are high, and in addition, the resistance is low, and therefore, the driving can be done without adding a very large force.

The deforming element is located in the inside of the tip-shaped container formed with the non-deforming wall, and therefore, the deformation of the deforming element is restrained, and the deformation can be done with a high degree of consistency.

Subsequently, FIG. 8 to FIGS. 12(a) and 12(b) illustrate a deforming element-included dispensing tip cartridge 115 according to a third embodiment of the present invention. In the deforming element-included dispensing tip cartridge 115, eight deforming element-included dispensing tips 113 arranged in a single line are integrally connected.

As shown in FIGS. 8 and 9, each deforming element-included dispensing tip 113 comprises a tip-shaped container 153 formed with a non-deforming wall having an opening portion 143b at an upper side and an inlet unit 133 at a lower side for allowing fluid to flow in and flow out, a sealing plug 193 adhered, using an adhesive agent and the like, and attached to the opening portion 143b so as to engage with and seal the opening portion 143b, and a hold-down plate 173 attached to the tip-shaped container 153 at the upper side of the sealing plug 193 and holding the sealing plug 193 from the upper side.

As shown in FIGS. 8 to 12(a) and 12(b), the tip-shaped container 153 comprises a deforming element containing portion 143 having the opening portion 143b and capable of accommodating the deforming element 123 so as to encompass a deformable range of the deforming element 123, a narrow tube portion 183 in communication with the deforming element containing portion 143 and having a diameter narrower than the deforming element containing portion 143 and having the inlet unit 133 that can be inserted into various kinds of external containers, and a transition unit 143a disposed between the narrow tube portion 183 and the deforming element containing portion 143. A flange 143c is provided outside of the opening portion 143b of the deforming element containing portion 143. For example, when the volume of each deforming element-included dispensing tip 113 is 250 microliters (which is in a range of medium volume), for example, the entire length in the axis direction is 75 mm, and the internal diameter of the deforming element containing portion 143 is 6 mm, and the internal diameter of the narrow tube portion is 0.85 mm.

These eight tip-shaped containers 153 are formed in a single line as a whole by connecting the deforming element containing portions 143 adjacent to each other with a non-deforming wall connection plate 115d. A rack loading projection portion 115a and a suspension projection portion 115b explained later further extending in the row direction and respectively engraved in two parallel non-deforming wall vertical plates disposed with a distance approximately equivalent to the external diameter of the deforming element containing portion 143 in the thickness direction of the cartridge 115 are respectively provided at both ends of the connection plate 115d. At the upper ends of the tip-shaped containers 153, eight tip-shaped containers 153 are connected in a single line by the container connection horizontal plate 115c provided with opening portions 143b. The tip-shaped container connection horizontal plate 115c is provided with multiple hold-down plate fixing holes (18 hold-down plate fixing holes 173d in this example) for attaching a hold-down plate 173 explained later.

The sealing plug 193 comprises a deforming wall formed with an elastic member such as rubber as the deforming element 123, and comprises a tubular wall projecting to the inside of the tip-shaped container 153 and comprising a depressions 123c surrounded by a bottom wall 123a and a side wall 123b. It should be noted that the transition unit 143a is formed in a tapered manner to become narrower toward the narrow tube portion 183 at the bottom inlet unit of the deforming element containing portion 143. Since the sealing plug 193 is attached to the opening portion 143b by adhesion, welding, and the like, the sealing plug 193 cannot be detached from the tip-shaped container 153. These eight sealing plugs 193 are connected with each other to form a sealing plug column 115e in a single line.

As shown in FIGS. 8 to 12(a) and 12(b), the hold-down plate 173 is attached to the tip-shaped container 153 at the upper side of the sealing plug 193, and the hold-down plate 173 is provided with an operation hole 173a corresponding to each sealing plug 193, and a tubular protection wall 173b formed so as to extend in the lower direction from the peripheral portion of the operation hole 173a. The eight hold-down plates 173 are coupled by a non-deforming wall to form a hold-down plate column 115f.

The hold-down plate column 115f is provided with a fixing claw 173c for attaching the hold-down plate column 115f to the tip-shaped container connection horizontal plate 115c.

FIG. 12 illustrates a used state where pins 200 serving as movable members explained later are inserted into deforming elements 123 of the deforming element-included dispensing tips 113 of the deforming element-included dispensing tip cartridge 115. For example, in FIG. 12(a), the pin 200 serving as the movable member is at the uppermost position in use, and reference numeral 1 denotes a liquid level in the maximum suction state. FIG. 12(b) is the lowermost positon when the pin 200 serving as the movable member is in use, and in this state, the liquid is completely discharged from each deforming element-included dispensing tip 113. A predetermined reference position is preferably an intermediate point of them both.

FIG. 13 illustrates a deforming element-included dispensing device 100 according to a fourth embodiment of the present invention. However, 96 deforming element-included dispensing tips 113 in which the eight deforming element-included dispensing tip cartridges 115 according to the third embodiment are arranged in 12 rows (columns) are in a state of being placed on the rack 220, and are not yet attached to the deforming element-included dispensing device 100. At both ends of the eight deforming element-included dispensing tip cartridge 115 in the arrangement direction (Y axis direction in the drawing) of the deforming element-included dispensing tips 113, rack loading projection portions 115a serving as second engagement units provided to protrude in the outer direction are engaged with depressed portions 221 formed on the rack 220 and the eight deforming element-included dispensing tip cartridge 115 is loaded on the rack 220. It should be noted that a suspension projection portion 115b serving as a first engagement unit provided at a first height position higher than the second height position of the second engagement unit is in a state capable of engaging with a support edge portion 273 of the frame body 270.

As shown in FIG. 13, the deforming element-included dispensing device 100 comprises a deforming element-included dispensing tip rack 220 accommodating the 12 eight deforming element-included dispensing tip cartridges 115 where the 96 deforming element-included dispensing tips 113 are arranged in a matrix form of 12 rows×8 columns (96 elements are arranged in parallel in two directions, i.e., 12 rows in the column direction and 8 columns in the row direction), a dispensing head 71 capable of supporting, at a time, 12 rows of the eight deforming element-included dispensing tip cartridges 115 accommodated in the deforming element-included dispensing tip rack 220 and sucking and discharging the liquid from the deforming element-included dispensing tips 113 or to the deforming element-included dispensing tips 113 by deforming the deforming wall of the deforming element 12 of each deforming element-included dispensing tip 113, the 96 microplates 30 serving as the container group which can accommodate various kinds of liquids, reagents, samples, and the like and in which multiple wells 32 (96 wells 32 in this example) are arranged in a matrix form, and an X axis moving mechanism 47 and a Z axis moving mechanism 48 serving as a head moving unit capable of respectively moving the dispensing head 700 with respect to the 96 microplates 30 serving as the container group in the X axis direction and the Z axis direction.

The X axis moving mechanism 47 comprises an X axis driving belt-like plate 475 extending in the X axis direction, two rails 474, i.e., upper and lower rails 474, disposed in parallel at the upper and lower sides of the front side along the X axis direction on the X axis driving belt-like plate 475, and four sliding unit 476 provided along the rails 474 in a slidable manner and engaging with the timing belt 473 to be able to move in the X axis direction with the timing belt 473, and a motor 471 for rotating and driving the timing belt 473 is provided at the back side of the X axis driving belt-like plate 475.

The four sliding units 476 are attached to the X axis moving body 477, and with the movement of the sliding unit 476, the X axis moving body 477 can move along the X axis. The X axis moving body 477 comprises the Z axis moving mechanism 48 for moving the dispensing head 71 along the Z axis, a dripping prevention mechanism 80 for preventing liquid from dropping from the deforming element-included dispensing tip 113, and the magnetic force unit 500 for giving magnetic force into the inside of the deforming element-included dispensing tip 113.

The Z axis moving mechanism 48 comprises a Z axis driving motor 481 attached to an upper plate 49 of the X axis moving body 477, a rotor 482 driven to rotate and driven by the Z axis driving motor 481, and a rotor 483 driven to rotate by the rotor 482 via the timing belt 484. The rotor 483 is coupled with a ball screw 485 extending in the lower direction, and with the rotation of the rotor 483, the ball screw 485 rotates. The ball screw 485 is screwed with an upper side substrate 74 constituting the dispensing head 71, and with the rotation and driving of the Z axis driving motor 481, the upper side substrate 74 constituting the dispensing head 71 can move along the guidance pillar 486 in the vertical direction. Likewise, in synchronization with the upper side substrate 74, the substrate 75 and a tip suspension unit are also driven in the vertical direction.

The upper side substrate 74 has a rotor 76 attached to a pin driving motor and is driven to rotate via a rotor 72 and a timing belt 73 driven to rotate by the pin driving motor, and the rotor 76 is coupled with a ball screw 66. The ball screw 66 is screwed with a pin driving upper plate 64, and the pin driving upper plate 64 is coupled with a pin arrangement plate 201 arranged with the 96 pins 200 arranged in the matrix form in such a manner that four connection pillars 65 penetrate through the substrate 75 of the dispensing head 71. When the pin driving upper plate 64 moves upward and downward according to the rotation of the pin driving motor, the pin arrangement plate 201 arranged with the 96 pins 200 moves upward and downward by means of the four connection pillars 65. Then, the pins 200 are inserted into pin holes 274 provided in the frame body 270 of the suspension unit attached to the substrate 75 of the dispensing head 71, and the deforming element of each deforming element-included dispensing tip 113 provided in association with the pin hole 274 can be deformed.

FIG. 14 enlarges and illustrates the main portion of the dispensing head 71. The suspension unit is attached to the substrate 75 of the dispensing head 71. The suspension unit comprises a frame body 270 capable of enclosing multiple deforming element-included dispensing tip cartridges 115 (12 deforming element-included dispensing tip cartridges 115 in this example) coupled with multiple deforming element-included dispensing tips 113 (eight deforming element-included dispensing tips 113 in this example) which are surrounded by three walls, i.e., an upper wall 272 corresponding to the upper surface portion and both side walls 271 corresponding to the both side surface portions, support edge portions 273 provided to be able to hold the suspension projection portions 115b serving as the first engagement unit provided at both ends disposed to protrude in the external direction along the row direction (longitudinal direction, Y axis direction) of the deforming element-included dispensing tip cartridge 115 so as to protrude in the inner side direction at the lower side of the both side walls 271 of the frame body 270, and pin holes 274 made through the upper wall 272 so that the pins 200 can be inserted into the positions corresponding to the deforming element-included dispensing tips 113, and the distance between the both side walls and the height and the depth of the both side walls are defined so that the multiple deforming element-included dispensing tip cartridges can be suspended in such a state that they are arranged in a matrix form.

Each support edge portion 273 is arranged with a fixed projection portion 275 or a depressed portion of the cartridge 115 having a length corresponding to an interval between a pair of suspension projection portions 115b engraved in the two parallel vertical plates provided for each cartridge 115 with an interval corresponding to the thickness of the deforming element-included dispensing tip cartridge 115 (approximately the external diameter of the deforming element containing portion in this example). Therefore, the cartridge 115 is supported by the frame body 270 provided with the suspension unit and can prevent deviation during deforming operation.

FIG. 14 further illustrates the dripping prevention mechanism 80. The dripping prevention mechanism 80 is provided on the X axis moving body 477, and does not move in the Z axis direction like the dispensing head 71. The dripping prevention mechanism 80 is provided to reciprocally move in the Y axis direction, and comprises a dripping prevention tray 81 capable of receiving droplets from each deforming element-included dispensing tip 113 suspended in such a manner that the tray 81 advances to the lower side of the frame body 270 provided with the suspension unit, and the tray 81 is coupled with a timing belt 82 stretched between a rotor 85 (see FIG. 15) driven to rotate by the driving motor 84 and a rotor 83, and moves according to the movement of the timing belt.

FIG. 15 illustrates a deforming element-included dispensing device 100 according to the fourth embodiment shown from the back side.

This shows a magnetic force unit 500. The magnetic force unit 500 is coupled with a base plate 75 of the dispensing head 71, and comprises a comb-shaped member driving motor 520 configured to drive, along the Y axis direction, six comb-shaped members 51 provided with eight magnets 511 on each of the front and back surfaces thereof in such a manner that the six comb-shaped members 51 can reciprocally move between every other adjacent deforming element-included dispensing tip cartridge 115, a rotor 530 driven to rotate by the comb-shaped member driving motor 520, and a timing belt stretched around the rotor.

Subsequently, operation of a deforming element-included dispensing device 100 according to an embodiment of the present invention will be explained with reference to FIGS. 12(a) and 12(b), 13, 16, and 17.

As shown in FIG. 13, first, the deforming element-included dispensing device 100 has the 12 eight deforming element-included dispensing tip cartridges 115 arranged in a matrix form on the rack 220. The deforming element-included dispensing tip cartridges 115 are loaded by engaging with totally 24 depressed portions 221 (see FIG. 16) where the rack loading projection portions 115a serving as the engagement units provided at both ends of the arrangement direction thereof are provided on the rack 220.

In step S1, the dispensing head 71 is moved in the X axis direction using the X axis moving mechanism 47. At this occasion, the height of the dispensing head 71 is controlled by the Z axis moving mechanism 48 so that the support edge portions 273 provided in a protruding manner in the inner side direction on the lower side of both side walls 271 of the frame body 270 provided with the suspension unit provided in the dispensing head 71 are located at the lower sides of the suspension projection portions 115b serving as the first engagement units provided at both ends of the deforming element-included dispensing tip cartridge 115 accommodated in the rack 220. It should be noted that the size of the both side wall 271 is formed so that the frame body 270 can cover the series of deforming element containing portions 143 of the deforming element-included dispensing tip cartridge 115.

In step S2, when the both side walls 271 and the upper wall 272 of the frame body 270 provided with the dispensing head 71 are located so that the series of deforming element containing portions of the deforming element-included dispensing tip cartridge 115 are surrounded by its three surfaces, and the suspension projection portion 115b is located above the space between the adjacent projection portions 275 provided on the support edge portion 273, the X axis moving mechanism 47 is stopped.

In step S3, when the Z axis moving mechanism 48 is controlled to move the dispensing head 71 to the upper side, the suspension projection portions 115b are supported by the support edge portions 273 of the frame body 270 and the deforming element-included dispensing tip cartridge is supported by the suspension unit by its own weight. Subsequently, the Z axis moving mechanism 48 moves the frame body 270 upward, so that the 12 eight deforming element-included dispensing tip cartridges 115 are moved at a time so that the inlet units 133 at the distal ends of the narrow tube portions are located above the rack 220.

In step S4, by driving the X axis moving mechanism 47, the X axis moving body 477 and the dispensing head 71 are located above the microplate 30. After the X axis moving body 477 is stopped, the Z axis moving mechanism 48 is controlled, so that the dispensing head 71 is lowered with respect to the X axis moving body 477, and the narrow tube portion of the deforming element-included dispensing tip 113 is inserted into each well 32 of the microplate 30.

In step S5, for example, a solution in which magnetic particles capturing DNA serving as the object substance extracted from a sample is accommodated in each well 32 of the microplate 30 in advance. In order to separate the object substance, the magnetic force unit 500 is driven to move the comb-shaped member 51 in the Y axis direction, so that the magnets 511 provided on the comb-shaped member 51 can come close to the narrow tube portions of the deforming element-included dispensing tips 113, and this causes the magnetic field to be given to the inside thereof. In this state, the pins 200 are moved upward and downward as shown in FIG. 12 by driving the pin driving motor to repeat the sucking and discharging of the magnetic particle suspension accommodated in the wells, so that the magnetic particles can be adsorbed to the inner wall of the narrow tube portion of each deforming element-included dispensing tip 113.

In step S6, in order to move the magnetic particles to the inside of the deforming element-included dispensing tip 113 while the magnetic particles are still adsorbed, the Z axis moving mechanism 48 is controlled to move the dispensing head 71 upward from the microplate 30 as shown in FIG. 17, and thereafter, the dripping prevention mechanism 80 is driven, so that the dripping prevention tray 81 is moved forward to the lower side of the deforming element-included dispensing tip cartridges 115, and the X axis moving mechanism 47 is used to move to the required position of the microplate.

FIGS. 18(*a*) to 18(*d*) illustrate carrier-enclosed deforming element-included dispensing tips 114, 114', 116, 116' having carriers enclosed therein according to a fifth embodiment of the present invention. These carrier-enclosed deforming element-included dispensing tips 114, 114', 116, 116' are formed such that the area having the carriers enclosed therein is formed separately from the main body and attached to the main body.

The carrier-enclosed deforming element-included dispensing tip 114 as shown in FIG. 18(*a*) comprises a tip-shaped container 154 formed with a non-deforming wall having an opening portion 144*b* at an upper side and an inlet unit 134 at a lower side for allowing fluid to flow in and flow out, and a sealing plug 194 attached by engaging with the opening portion 144*b* so as to seal the opening portion 144*b*, and the sealing plug 194 is provided with a deforming element 124 having a deforming wall urged to shrink in the upper direction and capable of extending in the lower direction in the tip-shaped container 154 in accordance with a pressing force in the lower direction along the axis line of the tip-shaped container 154 from the outside.

The tip-shaped container 154 comprises a deforming element containing portion 144 having the opening portion 144*b* and capable of accommodating the deforming element 124 so as to encompass a deformable range of the deforming element 124, a narrow tube portion 184 having a diameter narrower than the deforming element containing portion 144 and having the inlet unit 134 that can be inserted into various kinds of external containers, an accumulation portion 164 capable of accumulating liquid sucked from the inlet unit 134 in communication with the deforming element containing portion 144 and the narrow tube portion 184 and having a diameter that is thicker than the narrow tube portion 184 but is thinner than the deforming element containing portion 144, and a funnel-shaped transition unit 174' provided between the narrow tube portion 184 and the accumulation portion 164.

The narrow tube portion 184 has translucency, and the strip-shaped carriers 90 are enclosed so that the carriers 90 do not flow out of the area by processing the upper side choke portion and the lower side choke portion for the strip-shaped carriers 90 by swaging the narrow tube portion 184 so that the liquid can flow in and flow out but the carriers 90 cannot flow out. The upper side choke portion and the lower side choke portion correspond to a enclosing portion.

The upper end portion of the narrow tube portion 184 is engaged with an engagement unit 174*a* at the lower end of the transition unit 174, and is attached thereto by adhesion, thermal adhesion, ultrasonic adhesion, and the like. The narrow tube portion 184 is attached to the engagement unit 174*a* after the carriers 90 are enclosed inside thereof. The narrow tube portion 184 corresponds to an inner portion detection area, and is preferably formed with polypropylene that is a resin not emitting fluorescence and having a certain level of strength when the carriers 90 labelled with fluorescent pigment are measured.

As the deforming element 124, the sealing plug 194 comprises a deforming wall formed with an elastic member such as rubber, and comprises a tubular wall projecting to the inside of the tip-shaped container 154 and comprising a bottom wall 124*a* and a depression 124*c* surrounded by the side wall 124*b*. Reference numeral 144*a* is a bottom inlet unit of the deforming element containing portion 144, and is formed in a tapered manner to become narrower toward the accumulation portion 164. The sealing plug 194 is attached by engagement, and further, held by the hold-down plate 175 holding the sealing plug 194 from above, which makes the attachment more rigid. The hold-down plate 175 is provided with an operation hole 175*a* provided above the deforming element 124, and is provided with a protection wall 175*b* extending in the lower direction from the peripheral portion of the operation hole 175*a* so as to be surrounded by the deforming element 124 to prevent the deforming element 124 from wearing etc. The sealing plug 194 may be attached not only by engagement but also using adhesive agent, thermal adhesion, and the like.

In the carrier-enclosed deforming element-included dispensing tip 114' as shown in FIG. 18(*b*), particle-like carriers 91 are enclosed instead of the strip-shaped carriers 90 in the narrow tube portion 184 of the carrier-enclosed deforming element-included dispensing tip 114 explained in FIG. 18(*a*). The same elements as those in the carrier-enclosed deforming element-included dispensing tip 114 of FIG. 18(*a*) are denoted with the same reference numerals, and explanation thereabout is omitted.

In the carrier-enclosed deforming element-included dispensing tip 116 as shown in FIG. 18(*c*), a deforming element 125 is used instead of the deforming element 124 in FIG. 18(*a*). The deforming element 125 comprises a deforming wall formed with a flexible member, and comprises a tubular wall in a substantially circular tubular shape projecting to the inside of the tip-shaped container 154 and comprising a bottom wall 125*a* and a depression 125*c* surrounded by the side wall 125*b* a part of which is formed with bellows. The bellows is a deforming wall disposed on a portion of the side wall 125*b* of the deforming element 125 so as to divide the side wall 125*b* to an upper side and a lower side and configured to deform in such a manner that the vertical direction is the deforming direction. The bellows is in a screw shape, and as a wave form of the screw, crests (ten crests in this example) and roots (nine roots in this example) are formed. The sealing plug 195 may be attached with engagement or, in addition to engagement, the sealing plug 195 may be attached with adhesion, thermal adhesion, ultrasonic adhesion, and the like. In the case of adhesion and the like, the sealing plug 195 cannot be detached from the tip-shaped container 154.

In the carrier-enclosed deforming element-included dispensing tip 116' as shown in FIG. 18(*d*), particle-like carriers 91 are enclosed instead of the strip-shaped carriers 90 in the narrow tube portion 184 of the carrier-enclosed deforming element-included dispensing tip 116 explained in FIG. 18(*c*)

FIG. 19 illustrates carrier-enclosed deforming element-included dispensing tips 117, 117', 118, 118', 119, 119' in which carriers according to another example of the fifth embodiment of the present invention are enclosed. These carrier-enclosed deforming element-included dispensing tips 117, 117', 118, 118', 119, 119' are formed such that the area in which the carriers are enclosed is formed integrally with the main body.

The carrier-enclosed deforming element-included dispensing tip 117 as shown in FIG. 19(a) comprises a tip-shaped container 155 formed with a non-deforming wall having an opening portion 145b at an upper side and an inlet unit 135 at a lower side for allowing fluid to flow in and flow out, and a sealing plug 196 attached by engaging with the opening portion 145b so as to seal the opening portion 145b, and the sealing plug 196 is provided with a deforming element 126 having a deforming wall urged to shrink in the upper direction and capable of extending in the lower direction in the tip-shaped container 155 in accordance with a pressing force in the lower direction along the axis line of the tip-shaped container 155 from the outside.

The tip-shaped container 155 comprises a deforming element containing portion 145 having the opening portion 145b and capable of accommodating the deforming element 126 so as to encompass a deformable range of the deforming element 126, a narrow tube portion 185 in communication with the deforming element containing portion 145 and having a diameter narrower than the deforming element containing portion 145 and having the inlet unit 135 that can be inserted into various kinds of external containers, and a transition unit 145a disposed between the narrow tube portion 185 and the deforming element containing portion 145.

The narrow tube portion 185 has translucency, and the strip-shaped carriers 90 are enclosed so that the carriers 90 do not flow out of the area by processing the upper side choke portion and the lower side choke portion for the strip-shaped carriers 90 by swaging the narrow tube portion 184 so that the liquid can flow in and flow out but the carriers 90 cannot flow out. The upper side choke portion and the lower side choke portion correspond to a enclosing portion. The narrow tube portion 185 corresponds to the inner portion detection area.

As the deforming element 126, the sealing plug 196 comprises a deforming wall formed with an elastic member such as rubber, and comprises a tubular wall projecting to the inside of the tip-shaped container 155 and comprising a bottom wall 126a and a depression 126c surrounded by the side wall 126b. Reference numeral 145a is a bottom inlet unit of the deforming element containing portion 145, and is formed in a tapered manner to become narrower toward the narrow tube portion 185. The sealing plug 196 may be attached with engagement or, in addition to engagement, the sealing plug 196 may be attached with adhesion, thermal adhesion, ultrasonic adhesion, and the like. In the case of adhesion and the like, the sealing plug 196 may be attached with not only adhesion, but also thermal adhesion, ultrasonic adhesion, and the like. In these cases, the sealing plug 196 cannot be detached from the tip-shaped container 155. When the sealing plug 196 is attached, the hold-down plate 177 holding the sealing plug 196 from above is attached, which makes the attachment more rigid. The hold-down plate 177 is provided with an operation hole 177a provided above the deforming element 126, and is provided with a protection wall 177b extending in the lower direction from the peripheral portion of the operation hole 177a so as to be surrounded by the deforming element 126.

In the carrier-enclosed deforming element-included dispensing tip 117' as shown in FIG. 19(b), particle-like carriers 91 are enclosed instead of the strip-shaped carriers 90 in the narrow tube portion 185 of the carrier-enclosed deforming element-included dispensing tip 117 explained in FIG. 19(a).

The carrier-enclosed deforming element-included dispensing tip 118 as shown in FIG. 19(c) comprises a tip-shaped container 155 formed with a non-deforming wall having an opening portion 146b at an upper side and an inlet unit 136 at a lower side for allowing fluid to flow in and flow out, and a sealing plug 196 adhered, using an adhesive agent and the like, and engaging with the opening portion 146b to be attached thereto so as to seal the opening portion 146b, and the sealing plug 196 is provided with a deforming element 126 having a deforming wall urged to shrink in the upper direction and capable of extending in the lower direction in the tip-shaped container 156 in accordance with a pressing force in the lower direction along the axis line of the tip-shaped container 156 from the outside.

The tip-shaped container 156 comprises a deforming element containing portion 146 having the opening portion 146b and capable of accommodating the deforming element 126 so as to encompass a deformable range of the deforming element 126, a narrow tube portion 186 having a diameter narrower than the deforming element containing portion 146 and having the inlet unit 136 that can be inserted into various kinds of external containers, an accumulation portion 165 capable of accumulating liquid sucked from the inlet unit 136 in communication with the deforming element containing portion 146 and the narrow tube portion 186 and having a diameter that is thicker than the narrow tube portion 186 but is thinner than the deforming element containing portion 146, and a funnel-shaped transition unit 176 provided between the narrow tube portion 186 and the accumulation portion 165.

The accumulation portion 165 has translucency, and multiple cubic carriers 92 having diameters larger than the internal diameter of the narrow tube portion 186 and capable of capturing a predetermined substance by adsorption and the like to serve as a particle-like filling agent for chromatography are enclosed in the accumulation portion 165. The transition unit 176 has an elliptic shape in a cross section perpendicular to the axis direction, so that the transition unit 176 is not blocked by the cubic carriers 92. In this case, the "filling agent" is an insoluble stationary phase filled in a selected predetermined container in order to adsorb an object biological material included in a predetermined fluid serving as a so-called mobile phase on the basis of the principle of liquid chromatography.

In the carrier-enclosed deforming element-included dispensing tip 119 as shown in FIG. 19(d), a deforming element 127 is used instead of the deforming element 126 in FIG. 19(a). The deforming element 127 comprises a deforming wall formed with a flexible member, and comprises a tubular wall in a substantially circular tubular shape projecting to the inside of the tip-shaped container 155 and comprising a bottom wall 127a and a depression 127c surrounded by the side wall 127b a part of which is formed with bellows. The bellows is a deforming wall disposed on a portion of the side wall 127b of the deforming element 127 so as to divide the side wall 127b to an upper side and a lower side and configured to deform in such a manner that the vertical direction is the deforming direction. The bellows is in a screw shape, and as a wave form of a screw, crests (ten crests in this example) and roots (nine roots in this example) are formed.

In the carrier-enclosed deforming element-included dispensing tip 119' as shown in FIG. 19(e), particle-like carriers 91 are enclosed instead of the strip-shaped carriers 90 in the narrow tube portion 185 of the carrier-enclosed deforming element-included dispensing tip 119 explained in FIG. 19(d).

In the carrier-enclosed flat-shaped element-included dispensing tip 118' as shown in FIG. 19(f), the deforming element 127 is used instead of the deforming element 126 of the carrier-enclosed deforming element-included dispensing tip 118 explained in FIG. 19(c).

In FIGS. 18(a) to 18(d) and 19(a) to 19(f), reference numerals 114a, 117a, 118a denote suspension projection portions for suspending the tip from a dispensing tip head and the like.

Although not shown in the drawings, the carrier-enclosed deforming element-included dispensing tip can be of course integrated like the deforming element-included dispensing tip cartridge.

In order to measure the optical state in the carrier-enclosed deforming element-included dispensing tip, for example, the carrier-enclosed deforming element-included dispensing tip is provided in the dispensing head, and by using the light detection unit provided with the dispensing head, the optical state in the tip is measured by using one or more light reception terminals disposed in proximity to surround the periphery of the non-deforming portion at the outside of each carrier-enclosed deforming element-included dispensing tip. At this occasion, the light reception terminal is preferably movable relatively with respect to the tip.

Device examples will be shown in FIGS. 20(a), 20(b), 21(a), and 21(b) as such examples.

FIGS. 20(a) and 20(b) illustrate examples of a light detection unit 88 and magnetic force units 501, 502 according to the fifth embodiment used instead of the magnetic force units 50, 500 used with the deforming element-included dispensing devices 10, 100 suitable for a case where carrier-enclosed deforming element-included dispensing tips 114, 114', 116, 116', 117, 117', 118, 118', 119, 119' are used.

FIG. 20(a) is a perspective view illustrating only the magnetic force unit 501 and the light detection unit 88. The magnetic force unit 501 comprises three substantially square pillar-shaped comb-shaped members 521 which are as many as (the number of columns—1) of the carrier-enclosed deforming element-included tips and which are provided to be movable along the column direction between the adjacent columns of the carrier-enclosed deforming element-included dispensing tips having a column interval configured to be, e.g., twice a natural number of a column interval of the wells 32, i.e., a column interval configured to be "twice" and are provided to have such a width that the substantially square pillar-shaped comb-shaped members 521 extend along the column direction and can be inserted between adjacent columns of the carrier-enclosed deforming element-included dispensing tips, two substantially square pillar-shaped comb-shaped ends 521a, 521b provided outside of the comb-shaped member 521 and formed so as to slightly wider than the comb-shaped member 521, and a support member (not shown) coupled with one end of the comb-shaped member 521 and the comb-shaped ends 521a, 521b and extending in the row direction, and each of the comb-shaped members 521 and the comb-shaped end 521b comprises magnets 522 as many as the number of rows (12 magnets 522) with an interval configured to be the row interval of the wells 32 along the longitudinal direction, i.e., the column direction, and a guide rail 523 provided along the longitudinal direction, i.e., the column direction, of each of the comb-shaped members 521, 521a, 521b. The magnet 522 is provided at the same side surface side as the comb-shaped member 521 and the comb-shaped end 521b, and the guide rail 523 is provided at a position far from the side surface. The guide rail 523 guides the movement of the comb-shaped light detection unit 88 provided to be movable on the upper surfaces of the comb-shaped members 521, 521a, 521b. In this case, for example, the column interval or the row interval of adjacent carrier-enclosed deforming element-included dispensing tips are configured to be "twice" the column or row interval of the wells 32, but it is to be understood that they can be set to the same interval. In this case, it is to be understood that the number of comb-shaped members also change in accordance with the number of intervals and how the magnets and light detection holes explained later are arranged.

FIG. 20(b) is a perspective view illustrating an example of the magnetic force unit 502 and the light detection unit 88 according to another example of the fifth embodiment.

FIGS. 21(a) and 21(b) illustrate the details of the light detection unit 88, and the light detection unit 88 is provided to be movable relatively with respect to the magnetic force units 501, 502 on the magnetic force units 501, 502 provided with the dispensing heads 70, 71, and is configured to detect the state of the inside of each carrier-enclosed deforming element-included dispensing tip.

The light detection unit 88 comprises three substantially square pillar-shaped comb-shaped members 95 which are as many as (the number of columns—1) of the carrier-enclosed deforming element-included dispensing tips and which are provided to be movable with respect to the magnetic force units 501, 502 or the carrier-enclosed deforming element-included tip along the column direction between the adjacent carrier-enclosed deforming element-included tips having a column interval configured to be, e.g., twice a natural number of a column interval of the wells 32, i.e., a column interval configured to be "twice" and are provided to have such a width that the substantially square pillar-shaped comb-shaped members 95 extend along the column direction and can be inserted between adjacent columns of the carrier-enclosed deforming element-included dispensing tips, two substantially square pillar-shaped comb-shaped ends 95a, 95b provided outside of the comb-shaped member 95 and formed so as to slightly wider than the comb-shaped member 95, and a support member 96 coupled with one end of the comb-shaped member 95 and the comb-shaped ends 95a, 95b and extending in the row direction, and each of the comb-shaped members 95 and the comb-shaped ends 95a, 95b is provided with a light detection hole 98 penetrating and arranged along the row direction.

The light detection hole 98 provided on each of the comb-shaped members 95 and the comb-shaped ends 95a, 95b is provided with a distal end of the optical fiber 99 extending from the light emission unit 103, and the light detection hole 98 of an adjacent comb-shaped member 95 or the comb-shaped end 95a, 95b with a narrow and long gap interposed therebetween where the column of the carrier-enclosed deforming element-included dispensing tip is to be disposed is provided so that the distal end of the optical fiber 101 connected with the light sensor 102 faces the gap sandwiched by the comb-shaped members 95 or the two comb-shaped ends 95a, 95b adjacent to each other.

It should be noted that reference numeral 97 denotes a narrow groove provided with each of the comb-shaped members 95 and the comb-shaped ends 95a, 95b along the column direction engaging with and capable of sliding on the guide rail 523. The sizes and the shapes of the comb-shaped members 95 and the comb-shaped ends 95a, 95b and the support member 96 of the light detection unit 88 are respectively formed in sizes and shapes corresponding to the magnetic force units 501, 502.

Each of the embodiments explained above is to explain the present invention in a specific manner so that the present invention is understood more clearly, and each of the embodiments explained above does not limit other embodiments. Therefore, the embodiments can be changed without changing the gist of the invention. For example, in the embodiment, the volumes use ranges of volumes, i.e., a small volume (several dozen to 200 microliters), a medium volume (200 microliters to 1 milliliter), and a large volume (1 to 5 milliliters), but they are all examples, and the volume is not limited to each range. In order to drive the movable member, the movable member is directly driven using the linear step motor, but further, one end thereof may be axially supported, and the other end thereof may be driven using a link stick having a fulcrum at the intermediate point and driven in the vertical direction by a linear motor, or may be driven using a step motor and cam mechanism.

In the embodiment, an example where a tip arrangement holding unit is used in the tip support portion has been explained. However, if, with respect to the tray 22 corresponding to the tip arrangement holding unit, each deforming element-included dispensing tip 11 is considered to be integrally attached to the tray 22, this means that an example of a deforming element-included dispensing tip cartridge has been shown.

The shape of the deforming element-included dispensing tip is not limited to what has been described above, but the shape of the deforming element-included dispensing tip may have a step in the transition unit, or may have a step in a portion other than the transition unit.

The tip arrangement holding unit is not limited to an arrangement of a matrix form of 12 rows×8 columns explained above. For example, there are linear arrangements such as 4, 6, 8, 12 lines, and the like, or a matrix form with 24, 48, 384 lines, and the like, and arrangements of other shapes. The deforming element-included dispensing tip cartridge has been explained in a case of only eight lines, but is not limited thereto. For example, linear arrangements such as 4, 6, 12 lines, or deforming element-included dispensing tip cartridges are coupled with each other, and for example, there may be an arrangement in a matrix form of 12 rows×8 columns and the like.

The example of movement in the X axis and the Z axis has been explained, but it is to be understood that movement in the Y axis can also be added.

Further, the inlet unit of the narrow tube portion of the deforming element-included dispensing tip may be engaged with a short tube of which diameter is narrower such as those made of stainless and the like, so that the dispensing precision is enhanced.

In the above explanation, only the strip-shaped carriers, the particles-shaped carriers, and the cubic carriers have been explained as carriers. However, the embodiment is not limited to these carriers or the number thereof, and for example, block-shaped carriers, a single cub carrier, other numbers of particle-like carriers can be used.

The enclosing portion has been explained only in the case of swaging, but the embodiment is not limited thereto, and, for example, the projection portions protruding in the inner side direction and the enclosing portion formed separately can be used.

Expressions in terms of space explained above such as "upper side", "lower side", "bottom", "inside", "outside", "row", "column", "X", "Y", "Z", and the like used in the above explanation are given only for the drawings, and it is understood that these expressions do not limit the embodiments to a particular special direction or arrangement of the structure.

The above constituent elements, components, devices, and the like, for example, the tip-shaped container, the deforming element, the narrow tube portion, the accumulation portion, the container, the dispensing head, the sealing plug, the hold-down plate, the deforming element-included dispensing tip, the deforming element-included dispensing tip cartridge, the movable member, the magnetic force means, the movement mechanism, the carriers of the particle-like carrier, the strip-shaped carrier, and the like (the carriers are not limited thereto), enclosing portion, and the like may be combined in any way while deforming as appropriately.

INDUSTRIAL APPLICABILITY

The deforming element-included dispensing tip, the deforming element-included dispensing device, and the deforming element-included dispensing processing method according to the present invention are related to fields requiring processing of various kinds of solutions, for example, various kinds of fields such as industrial fields, food, agricultural, agriculture fields such as fish processing, pharmaceutical fields, medical field dealing with health, insurance, immunity, disease, genetic, and the like, fields such as chemical or biology. In particular, the present invention is effective in a case of sequentially executing a series of processing using many reagents and substances with processing in a predetermined order.

REFERENCE SIGNS LIST

10, 100 deforming element-included dispensing device
11, 11', 110, 111, 112, 113 deforming element-included dispensing tip
115 deforming element-included dispensing tip cartridge
114, 116, 117, 118, 119 carrier-enclosed deforming element-included dispensing tip
12, 120, 121, 122, 123, 124, 125, 126, 127 deforming element
15, 150, 151, 152, 153, 154, 155 tip-shaped container
20, 200 pin (movable member)
30 microplate
50, 500, 501, 502 magnetic force unit
70, 71 dispensing head
88 light detection unit
90, 91, 92 carrier

The invention claimed is:

1. A deforming element-included dispensing tip cartridge, comprising:
   a plurality of tip-shaped containers formed with a non-deforming wall so as to be integrally coupled and provided with a plurality of opening portions at an upper side and provided with a plurality of inlet units at a lower side for allowing fluid to flow in and flow out; and
   a plurality of sealing plugs attached to the opening portions so as to seal the opening portions,
   wherein the sealing plug is provided with a deforming element that has a deforming wall that is formed so as to be able to extend in a lower direction in each of the tip-shaped containers in accordance with pressing from an outside and is formed so as to be urged to shrink or so as to be able to shrink in an upper direction, and the deforming element is formed so as to be located inside each of the tip-shaped containers, wherein the sealing plug has a depression surrounded by a tubular wall projecting to an inside of the tip-shaped container as the deforming element, and the tubular wall comprises a bottom wall on which force is exerted from an outside to extend the deforming element, and a side wall having at least the deforming wall; and wherein the deforming element-included dispensing tip cartridge further comprises a hold-down plate attached to the tip-shaped containers at the upper side of the sealing plugs and holding the sealing plugs from the upper side, and the hold-down plate is provided with an operation hole in association with each of the sealing plugs, and a protection wall formed so as to extend in the lower direction from the peripheral portion of the operation hole and so as to be surrounded by the deforming element.

2. The deforming element-included dispensing tip cartridge according to claim 1, wherein in a state of capable of coming into contact with a fluid that flows in and out through the inlet unit, a carrier bonded with or capable of being bonded with a predetermined substance is enclosed in an inner portion detection area which is inside of the tip-shaped container.

3. A deforming element-included dispensing tip cartridge, comprising:

a plurality of tip-shaped containers formed with a non-deforming wall so as to be integrally coupled and provided with a plurality of opening portions at an upper side and provided with a plurality of inlet units at a lower side for allowing fluid to flow in and flow out; and a plurality of sealing plugs attached to the opening portions so as to seal the opening portions, wherein the sealing plug is provided with a deforming element that has a deforming wall that is formed so as to be able to extend in a lower direction in each of the tip-shaped containers in accordance with pressing from an outside and is formed so as to be urged to shrink or so as to be able to shrink in an upper direction, and the deforming element is formed so as to be located inside each of the tip-shaped containers, wherein the sealing plug has a depression surrounded by a tubular wall projecting to an inside of the tip-shaped container as the deforming element, and the tubular wall comprises a bottom wall on which force is exerted from an outside to extend the deforming element, and a side wall having at least the deforming wall; and wherein the deforming element-included dispensing tip cartridge is provided with two engagement units which are a first engagement unit and a second engagement unit which are provided in a projecting manner or in a recessed manner with respect to an external direction at both ends along the arrangement direction thereof, and the first engagement unit is disposed at a first height, and the second engagement unit is disposed at a second height lower than the first height.

4. The deforming element-included dispensing tip cartridge according to claim 3, wherein in a state of capable of coming into contact with a fluid that flows in and out through the inlet unit, a carrier bonded with or capable of being bonded with a predetermined substance is enclosed in an inner portion detection area which is inside of the tip-shaped container.

* * * * *